(12) United States Patent
Christensen

(10) Patent No.: US 11,497,842 B2
(45) Date of Patent: Nov. 15, 2022

(54) BODILY FLUID DRAINAGE ASSEMBLY

(71) Applicant: SteriGear, LLC, Provo, UT (US)

(72) Inventor: Earl G. Christensen, Alpine, UT (US)

(73) Assignee: SteriGear, LLC, Provo, UT (US)

( * ) Notice: Subject to any disclaimer, the term of this patent is extended or adjusted under 35 U.S.C. 154(b) by 0 days.

(21) Appl. No.: 16/773,611

(22) Filed: Jan. 27, 2020

(65) Prior Publication Data

US 2020/0155735 A1   May 21, 2020

Related U.S. Application Data

(63) Continuation of application No. 14/444,271, filed on Jul. 28, 2014, now Pat. No. 11,090,415, which is a (Continued)

(51) Int. Cl.
| | | |
|---|---|---|
| *A61M 5/00* | (2006.01) | |
| *A61M 1/00* | (2006.01) | |
| *A61F 5/44* | (2006.01) | |
| *A61J 1/10* | (2006.01) | |
| *A61J 1/14* | (2006.01) | |
| *A61J 1/22* | (2006.01) | |
| *G01N 11/00* | (2006.01) | |
| *G01N 33/20* | (2019.01) | |
| *B65D 79/00* | (2006.01) | |

(52) U.S. Cl.
CPC ................ *A61M 1/69* (2021.05); *A61F 5/44* (2013.01); *A61J 1/10* (2013.01); *A61J 1/1462* (2013.01); *A61J 1/1487* (2015.05); *A61J 1/22* (2013.01); *A61J 1/1468* (2015.05); *A61M 2205/583* (2013.01); *Y10T 156/10* (2015.01)

(58) Field of Classification Search
CPC .......... A61M 5/00; A61M 1/00; G01N 11/00; G01N 33/20; B65D 79/00
See application file for complete search history.

(56) References Cited

U.S. PATENT DOCUMENTS

| | | |
|---|---|---|
| D200,807 S | 4/1965 | Mason |
| 3,253,593 A | 5/1966 | Cronin, Jr. |

(Continued)

FOREIGN PATENT DOCUMENTS

| | | |
|---|---|---|
| JP | 5337986 B2 * | 12/2007 |
| KR | 1020049022170 A | 3/2004 |
| WO | 2010045042 | 4/2010 |

OTHER PUBLICATIONS

European Search Report dated Feb. 20, 2018 for EP application 09821003.

(Continued)

*Primary Examiner* — Tatyana Zalukaeva
*Assistant Examiner* — Ilya Y Treyger
(74) *Attorney, Agent, or Firm* — Thorpe North and Western, LLP; David W. Osborne

(57) ABSTRACT

A bodily fluid drainage assembly can include a fluid bag and one or more covers. The assembly can include one or more volume indicators from which an approximate volume of a bodily fluid that is retained within the bag can be ascertained. In some arrangements, a cover includes a volume indicator that defines an opening through which a transparent or semitransparent portion of the bag can be viewed.

19 Claims, 22 Drawing Sheets

Related U.S. Application Data continuation of application No. 13/088,409, filed on Apr. 17, 2011, now Pat. No. 8,790,320, which is a continuation-in-part of application No. 12/253,714, filed on Oct. 17, 2008, now Pat. No. 8,092,436, and a continuation-in-part of application No. PCT/US2009/059482, filed on Oct. 5, 2009, and a continuation-in-part of application No. 12/253,714, filed on Oct. 17, 2008, now Pat. No. 8,092,436.

(60) Provisional application No. 61/143,327, filed on Jan. 8, 2009, provisional application No. 61/184,240, filed on Jun. 4, 2009.

(56) References Cited

U.S. PATENT DOCUMENTS

| | | |
|---|---|---|
| 3,601,125 A | 8/1971 | Moss |
| D221,911 S | 9/1971 | Ericson |
| D227,184 S | 6/1973 | Stevens |
| 3,973,565 A | 8/1976 | Steer |
| 4,095,589 A | 6/1978 | Manschot et al. |
| 4,122,851 A | 10/1978 | Grossner |
| 4,153,163 A | 5/1979 | Alderman et al. |
| 4,173,979 A | 11/1979 | Odis |
| 4,312,352 A | 1/1982 | Meisch |
| 4,343,316 A | 8/1982 | Jespersen |
| 4,417,892 A | 11/1983 | Meisch |
| 4,460,362 A | 7/1984 | Bates |
| 4,496,354 A | 1/1985 | Steer et al. |
| 4,526,576 A | 7/1985 | Cianci |
| 4,562,984 A | 1/1986 | Sherlock |
| 4,606,736 A | 8/1986 | Van den Weghe |
| 4,625,734 A | 12/1986 | Sherlock |
| D296,360 S | 6/1988 | Oelberg |
| 4,874,387 A | 10/1989 | Boone |
| 4,936,837 A | 6/1990 | Wexler |
| D310,721 S | 9/1990 | Beisdang, III |
| 5,046,195 A | 9/1991 | Koritan |
| 5,056,685 A | 10/1991 | Wild |
| 5,211,642 A | 5/1993 | Clendenning |
| 5,226,564 A | 7/1993 | Steer et al. |
| 5,263,946 A | 11/1993 | Klug |
| 5,454,797 A | 10/1995 | Haswell |
| 5,489,281 A | 2/1996 | Watanabe et al. |
| 5,496,299 A | 3/1996 | Felix et al. |
| D369,662 S | 5/1996 | Kuentz |
| 5,531,724 A | 7/1996 | Young |
| D375,355 S | 11/1996 | Bierman |
| D377,115 S | 1/1997 | Feriend et al. |
| 5,686,096 A | 11/1997 | Khan et al. |
| D391,483 S | 3/1998 | Freeman |
| 5,725,515 A | 3/1998 | Propp |
| 5,759,180 A | 6/1998 | Myhres |
| D398,990 S | 9/1998 | Briggs et al. |
| 6,053,905 A | 4/2000 | Daignault, Jr. et al. |
| 6,096,007 A | 8/2000 | Haan et al. |
| 6,132,407 A | 10/2000 | Genese et al. |
| D438,616 S | 3/2001 | Williams |
| 6,261,254 B1 | 7/2001 | Baron et al. |
| D458,687 S | 6/2002 | Dale et al. |
| 6,482,190 B1 | 11/2002 | Genese et al. |
| D467,414 S | 12/2002 | Pavlu et al. |
| D470,586 S | 2/2003 | Felstet |
| 6,612,432 B2 | 9/2003 | Motson |
| 6,613,036 B1 | 9/2003 | Farmer et al. |
| D482,063 S | 11/2003 | Jones et al. |
| 6,709,420 B1 | 3/2004 | Lincoln et al. |
| D502,557 S | 3/2005 | O'Dell |
| 6,955,272 B2 | 10/2005 | Collins |
| D515,699 S | 2/2006 | Girod |
| 7,001,370 B2 | 2/2006 | Kubalak et al. |
| D537,948 S | 3/2007 | Smith |
| D563,552 S | 3/2008 | Bierman et al. |
| D577,437 S | 9/2008 | Bierman et al. |
| 7,500,968 B1 | 3/2009 | Nappa et al. |
| 7,513,894 B2 | 4/2009 | Howlett |
| D601,707 S | 10/2009 | Chouiller |
| 7,645,968 B2 | 1/2010 | Salvadori et al. |
| D609,802 S | 2/2010 | Harren |
| D612,060 S | 3/2010 | Smith |
| D612,937 S | 3/2010 | Christensen |
| D621,926 S | 8/2010 | Christensen |
| 8,092,436 B2 | 1/2012 | Christensen |
| D673,266 S | 12/2012 | Tufts et al. |
| 8,361,044 B2 | 1/2013 | Marshall |
| D684,687 S | 6/2013 | Christensen |
| D684,688 S | 6/2013 | Christensen |
| 2002/0077609 A1 | 6/2002 | Johnson |
| 2003/0060786 A1 | 3/2003 | Olsen et al. |
| 2004/0147887 A1 | 7/2004 | Hagstroem et al. |
| 2004/0236293 A1 | 11/2004 | Tanghoj et al. |
| 2004/0240520 A1 | 12/2004 | Faries et al. |
| 2005/0059952 A1 | 3/2005 | Giuliano et al. |
| 2006/0111681 A1 | 5/2006 | Vernon |
| 2007/0203463 A1* | 8/2007 | Salvadori ............ A61F 5/4404 604/323 |
| 2007/0203464 A1 | 8/2007 | Green et al. |
| 2007/0282296 A1 | 12/2007 | Matsuda et al. |
| 2009/0024099 A1 | 1/2009 | Burgess et al. |
| 2009/0030386 A1 | 1/2009 | Kim et al. |
| 2009/0036861 A1 | 2/2009 | Moy et al. |
| 2009/0088709 A1 | 4/2009 | Salvadori |
| 2012/0041400 A1 | 2/2012 | Christensen |

OTHER PUBLICATIONS

International Search Report and Written Opinion dated Apr. 27, 2010 for international application PCT/US2009/059482.
"Drainage Bag Cover", Western Home Medical; www.westernhomemedical.com/product.jsp?product_id=83; accessed May 30, 2008 (1 page).
"Privacy Cover for Urinary Drainage Bags; Access to Recreation", www.store.accesstr.com/Detail.bok?no=1789; accessed May 30, 2008 (1 page).
"SteriGear Fig Leaf Urinary Drain Bag", as shown on http://long-term-care.advancedweb.com, dated Oct. 2, 2009 (2 pages).
"Urinary Drain Bag with Fig Leaf Cover by SteriGear", Urinary Drain Bag with Fig Leaf Cover by SteriGear as shown on www.SteriGear.com, viewed Jan. 13, 2010 (1 page) pub date unknown.
"Urine Drain Bag Holder", http://cgi.ebay.ca/Urine-Drain-bag-holder-Disceet-Catheter-Bag-Cover_WOQQitemZ320 . . . ; accessed May 30, 2008 (4 pages).
Christensen , Notice of Allowance dated Dec. 14, 2015 for U.S. Appl. No. 29/534,458.
Christensen , Notice of Allowance dated Feb. 14, 2013 for U.S. Appl. No. 29/390,343.
Christensen , Notice of Allowance dated Feb. 14, 2013 for U.S. Appl. No. 29/390,346.
Christensen , Notice of Allowance dated Mar. 20, 2014 for U.S. Appl. No. 13/088,409.
Christensen , Notice of Allowance dated Sep. 29, 2011 for U.S. Appl. No. 12/253,714.
Christensen , Office Action dated Apr. 11, 2014 for U.S. Appl. No. 29/390,348.
Christensen , Office Action dated Aug. 7, 2019 for U.S. Appl. No. 14/444,271.
Christensen , Office Action dated Dec. 16, 2013 for U.S. Appl. No. 13/088,409.
Christensen , Office Action dated Jan. 25, 2019 for U.S. Appl. No. 14/444,271.
Christensen , Office Action dated Jan. 29, 2015 for U.S. Appl. No. 29/390,348.
Christensen , Office Action dated Jul. 25, 2013 for U.S. Appl. No. 29/390,348.
Christensen , Office Action dated Jul. 27, 2017 for U.S. Appl. No. 14/444,271.
Christensen , Office Action dated Oct. 18, 2016 for U.S. Appl. No. 14/444,271.

(56) References Cited

OTHER PUBLICATIONS

Christensen, Office Action dated Sep. 12, 2013 for U.S. Appl. No. 13/088,409.
Christensen, Office Action dated Feb. 13, 2020 for U.S. Appl. No. 14/444,271.

* cited by examiner

BODILY FLUID DRAINAGE ASSEMBLY

CROSS-REFERENCE TO RELATED APPLICATIONS

The present application is a continuation of pending U.S. patent application Ser. No. 14/444,271, filed on Jul. 28, 2014, which is a continuation of U.S. patent application Ser. No. 13/088,409, filed on Apr. 17, 2011, which issued as U.S. Pat. No. 8,790,320 on Jul. 29, 2014, which is a continuation-in-part of U.S. patent application Ser. No. 12/253,714, filed on Oct. 17, 2008, which issued as U.S. Pat. No. 8,092,436 on Jan. 10, 2012, and is also a continuation-in-part of International Application No. PCT/US2009/059482, which has an international filing date of Oct. 5, 2009, was published as International Publication No. WO 2010/045042, and claims priority to: U.S. Provisional Patent Application No. 61/143,327, filed on Jan. 8, 2009; U.S. Provisional Patent Application No. 61/184,240, filed on Jun. 4, 2009; and U.S. patent application Ser. No. 12/253,714, filed on Oct. 17, 2008. The entire contents of each of the foregoing applications and patents are hereby incorporated by reference herein.

TECHNICAL FIELD

The present disclosure relates generally to the field of medical devices. More specifically, the present disclosure relates to bodily fluid drainage assemblies.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the disclosure's scope, the embodiments will be described and explained with specificity and detail in reference to the accompanying drawings.

DETAILED DESCRIPTION

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the disclosure, as claimed, but is merely representative of various embodiments. While the various aspects of the embodiments are presented in drawings, the drawings are not necessarily drawn to scale unless specifically indicated.

The phrases "connected to," "coupled to" and "in communication with" refer to any form of interaction between two or more entities, including mechanical, electrical, magnetic, electromagnetic, fluid, and thermal interaction. Two components may be coupled to each other even though they are not in direct contact with each other. The term "abutting" refers to items that are in direct physical contact with each other, although the items may not necessarily be attached together.

Figure 1:
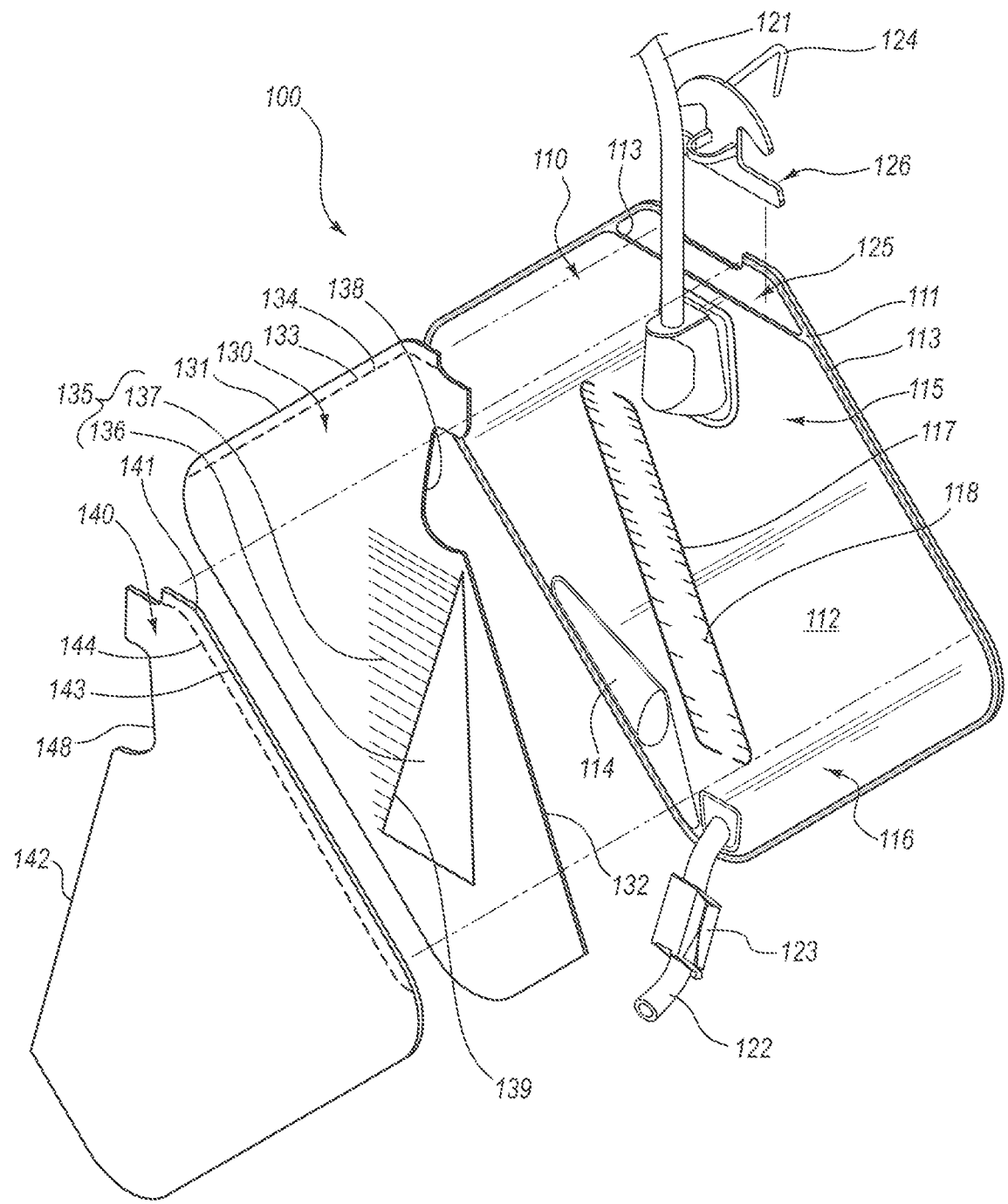
FIG. 1 is an exploded perspective view of a bodily fluid drainage assembly.
Figure 2:
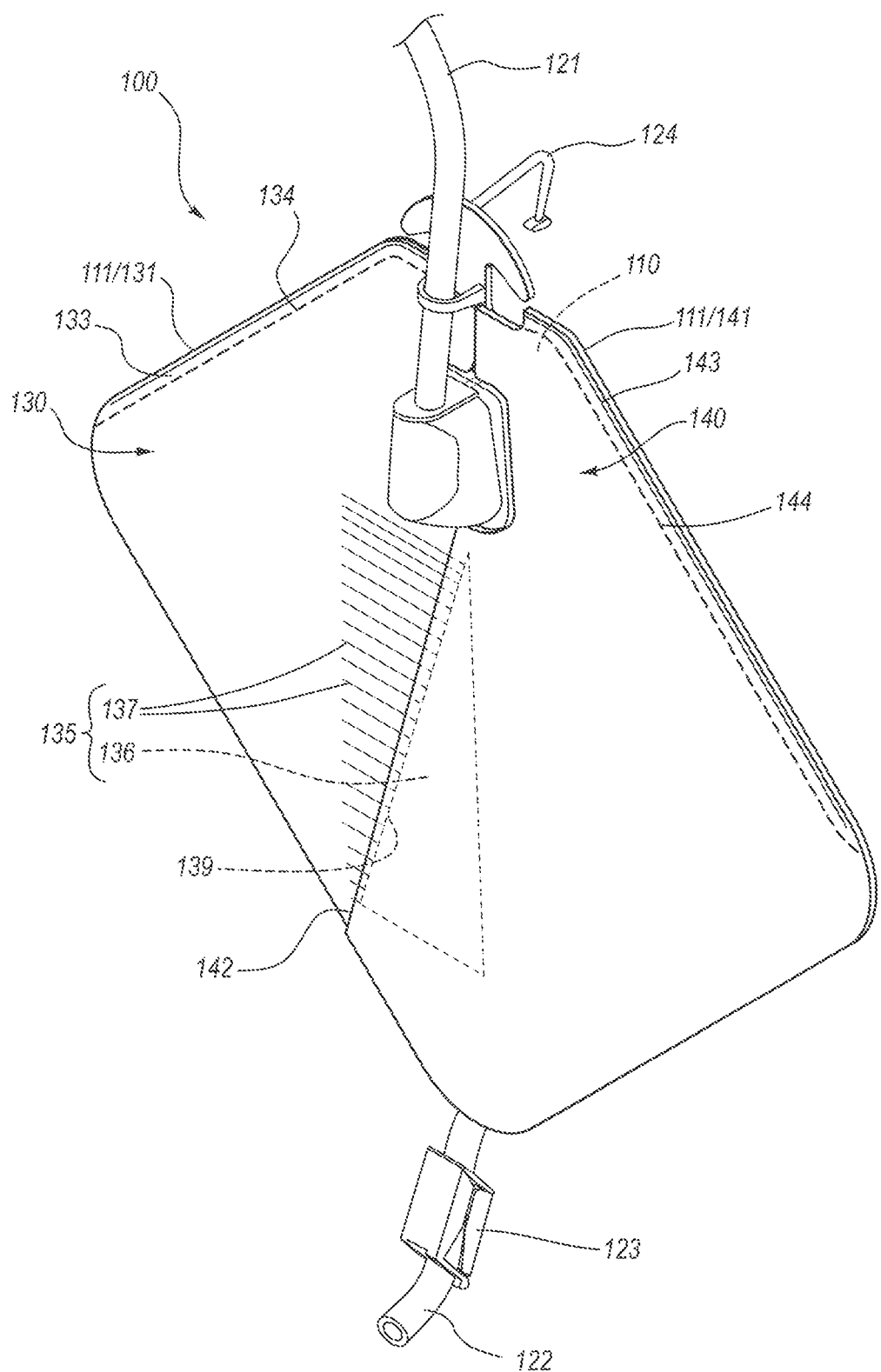
FIG. 2 is a perspective view of the bodily fluid drainage assembly of FIG. 1 after the assembly has been assembled.

FIGS. 1-2 depict a bodily fluid drainage assembly 100, from front views, wherein FIG. 1 is an exploded-perspective view and FIG. 2 is a perspective view after the assembly has been assembled. Bodily fluid drainage assembly 100 may comprise a fluid bag 110, a first cover 130 and a second cover 140. Assembly 100 is configured to receive bodily fluid; optionally retain the fluid; at least partially obscure the visibility of the fluid while allowing an approximate volume of the fluid to be determined; and optionally allow the fluid to be directly viewed by at least partially removing a portion of the assembly. Drainage bag 110 and first and second covers 130, 140 may comprise polyvinyl chloride, polyurethane, vinyl or any other suitable material. In some embodiments, one or more of the drainage bag 110 and the first and second covers 130, 140 may comprise the same material, whereas in other embodiments, one or more of the drainage bag 110 and the first and second covers 130, 140 may comprise different materials.

Drainage bag 110 may comprise one or more panels 112 of one or more liquid impervious materials. At least a portion of the front panel 112 can be substantially transparent or semitransparent such that a liquid contained within the bag may be readily observed. The panels 112 may be joined along an outer edge 111 thereof via radio frequency (RF) welding, heat sealing, gluing, or any other suitable technique. Once joined, the two panels comprise a seam 113 adjacent to outer edge 111. When coupled together, the panels 112 form a fillable void that may receive fluid via an inlet tube 121 and a corresponding inlet aperture (not visible) that are located on upper portion 115 of bag 110. Approximate volume of fluid within the bag 110 may be ascertained via a first volume indicator 117, which may comprise marks or graduations 118 on front panel 112 of bag 110. In the depicted embodiment, graduations 118 denote various predetermined volumes and may be printed on the fluid bag. In another embodiment, the graduations 118 may comprise raised or recessed portions of the fluid bag that are formed during or after manufacturing of the fluid bag. The graduations 118 may represent any predetermined measurement of volume, such as fluid ounces and/or milliliters, and may vary in their relative distributions accordingly. In some embodiments, the space between sequential graduations 118 may not be uniform in scale so as to account for a non-linear rate of rise in fluid level, such as may result from expansion of the fluid bag 110 as the bag fills with liquid and/or from a transverse dimension of the bag 110 that varies with a height of the bag. In the depicted embodiment, graduations 118 are located on a left portion (as seen from the viewer's perspective) of fluid bag 110; however, in other embodiments, the graduations may be located at any suitable location on fluid bag 110. Stated otherwise, in the illustrated embodiment, the first volume indicator 117 extends upwardly and at a leftward slanting angle. Since at least a portion of front panel 112 is transparent or semitransparent (e.g., translucent), the top of the fluid can be compared to the graduations 118 to thereby determine the volume of the fluid, or the approximate volume thereof.

A variety of types and configurations of fluid bags can be utilized without departing from the scope and spirit of the present disclosure. For example, the fluid bag may be manufactured using a one-piece method, wherein the bag comprises a single piece of plastic that is folded along one or more edges and, further, is sealed to itself or otherwise closed along one or more edges. Further, the shape and size of assembly 100 is primarily for illustrative purposes and may vary.

A hanger 124 can be located at an upper portion 115 of the fluid bag 110, such as within a non-fillable region 125 of the fluid bag 110. For example, in the illustrated embodiment, a base region 126 of the hanger 124 can be positioned within the non-fillable region 125 of the fluid bag 110 (e.g., a region that is not configured to be filled with fluids from a patient) and can be retained in this position by the portions of the seam 113 that define the edges of the non-fillable region 125. In some embodiments, the base region 126 of the hanger 124 is placed between the front and rear panels 112 prior to formation of the seam 113, and the seam 113 is thereafter formed so as to encompass the base region 126 of the hanger 124. In other embodiments, the base region 126 of the hanger 124 may be inserted into a previously formed non-fillable region 125.

Hanger 124 can be configured to allow assembly 100 to be suspended from a patient, or from a nearby structure, such as a wheelchair, bed, or stand. Hanger 124 may comprise one or more hook-like extensions, one or more apertures, or both. The hanger 124 may comprise one or more pieces of plastic, and in some embodiments, may be fixedly coupled to assembly 100 via RF welding, heat sealing, gluing, hardware, or any other suitable technique. In other embodiments, hanger 124 may be coupled to assembly 100 such that it may be selectively removed from the fluid bag 110. In other embodiments, hanger 124 may comprise an aperture in bag 110 and/or first and second covers 130 and 140. Still other arrangements of the hanger 124 are possible.

An outlet tube 122 and corresponding drainage bag outlet aperture (not visible) are located at the bottom portion 116 of the fluid bag 110. The outlet tube 122 may allow a fluid contained within the fluid bag 110 to be drained from the bag or retained within the bag via an output regulator 123. Output regulator 123 may comprise a plastic or metal clip, in-line valve, or any other suitable structure. Fluid bag 110 may further comprise an outlet tube holder 114 that comprises a slot, loop, or hook that is configured to receive and reversibly retain outlet tube 122 in an at least partially upright position. For example, in the illustrated embodiment, the outlet tube holder 114 comprises a plastic piece that projects forwardly from the fluid bag 110 so as to define a cavity. When the assembly 100 is in a packaged or pre-use state, a bottom end of the outlet tube 122 can be positioned within the cavity of the outlet tube holder 114. The outlet tube 122 can be removed from the holder 144 and allowed to hang downwardly into the positions shown in FIGS. 1 and 2 during use of the assembly 100.

As will be determined by those skilled in the art, a variety of types and configurations of bodily fluid drainage bags can be utilized without departing from the scope and spirit of the present disclosure. For example, the size, shape, and proportions of the fluid bag may vary (see, e.g., FIGS. 6-9). Additionally, the size, shape, and proportions of the inlet and outlet tubes, as well as the materials from which the fluid bag and tubes are manufactured may vary. For example, in some embodiments, the hanger comprises a contiguous extension of the bag, whereas in other embodiments, the hanger comprises an aperture in the bag.

Bodily fluid drainage assembly 100 may further comprise a first cover 130 that can be formed from or otherwise include an opaque material (or at least partially opaque material capable of obscuring the appearance of a fluid positioned at one side thereof), and which may define a similar shape as fluid drainage bag 110. First cover 130 has an outer edge 131 that may be at least partially aligned with outer edge 111 of fluid bag 110. However, at least a portion of the outer edge 131 of the first cover 130 may extend outwardly beyond the outer edge 111 of the fluid drainage bag 110. When first cover 130 is coupled to bag 110, a seam 133 may be formed along (e.g., at or near) outer edge 111. The first cover may be coupled to the fluid drainage bag via RF welding, heat sealing, gluing, hardware, or any other suitable technique. First cover 130 may be coupled to bag 110 only along (e.g., at or near) outer edge 131, or in other embodiments, the first cover 130 can be coupled to the bag 110 along more than one edge.

In the illustrated embodiment, the cover 130 further comprises perforations 134 that are located adjacent to seam 133 and are configured to allow cover 130 to be at least partially removed from bag 110. The perforations 134 may thus define a region of weakness. In other embodiments, the seam 133 itself, or a portion of the first cover 130 that borders the seam 133, may define a region of weakness for the cover 130 (i.e., a region at which the cover 130 is weaker than neighboring portions thereof), such that the cover 130 may be removed from the bag 110 generally along the line or contour of the seam 133. Other suitable methods and systems for removing the cover 130 are also possible.

First cover 130 further comprises an interior edge 132 that may have a notch or cutout 138 that partially surrounds the junction of inlet tube 121 and fluid bag 110. A second volume indicator 135 is located on first cover 130. In the illustrated embodiment, the second volume indicator 135 comprises a fluid level indicator 136 and graduations 137. As can readily be seen in FIGS. 1 and 2 and determined from other disclosures herein, the fluid level indicator 136 and the graduations 137 can be printed on the first cover 130 in any suitable manner so as to be readily visually discernible relative to the adjacent portions of the first cover 130, and/or may comprise raised or indented portions that are readily visually discernable. In the illustrated embodiment, the lines of the graduations 137 are substantially horizontal. Each of the lines of the graduations 137 extends from a linear edge 139 of the fluid level indicator 136. In the illustrated embodiment, the linear edge 139 is angled (non-perpendicularly) relative to the lines of the graduations 137. Moreover, as shown in FIG. 2B, when the covers 130, 140 are in an initial state (e.g., when the bag 110 is empty), the cover 140 can extend over the linear edge 139, and the inner edge 142 of the cover 140 can be angled by a different amount relative to the graduations 137, as compared with the linear edge 139. The function of second volume indicator 135 is described in text associated with FIGS. 3A-3B, below. It will be appreciated that in other embodiments, the edge 139 may define some contour other than linear.

Second cover 140 may comprise an opaque material that may be identical to that of the first cover 130. The second cover 140 may comprise an outer edge 141, an inner edge 142, a seam 143, perforations 144, and a cutout 148. As with first cover 130, second cover 140 may be coupled to bag 110 along outer edge 141 to form seam 143. Perforations 144 may be formed in cover 140 along the seam 143 such that the cover may be at least partially removed. In other or further embodiments, a region of weakness may be defined by or may border the seam 143 such that the second cover 140 may be removed generally along the line or contour of the seam 143. First and second covers 130 and 140 may be coupled to fluid bag 110 during manufacture of the bag 110. For example, the seams 133 and/or 143 may be formed at the same time.

A variety of types and configurations of first and second covers 130, 140 may be used without deviating from the spirit of the present disclosure. For example, the first and second covers 130, 140 may or may not be coupled to the lower portion of the fluid bag 110. In other or further embodiments, the covers 130, 140 may not extend all the way to the bottom of the fluid bag 110. First and second covers 130, 140 may be configured to be removable without employing perforations; for example, the seams may be configured to rupture when tension is applied for them or reversible (e.g., selectively attachable) fasteners may be used such as snaps, clips, zippers, hooks and loops closures, or removable glue. The fasteners may instead permanently or non-removably fix the covers 130, 140 to the fluid bag 110. The various forms of fastening the covers 130, 140 to the bag 110 may additionally or alternatively be used to attach the covers 130, 140 to other portions of the assembly 100. For example, in some embodiments, at least a portion of one or more of the covers 130, 140 may be attached to the hanger 124 in any suitable manner.

Figure 3A:
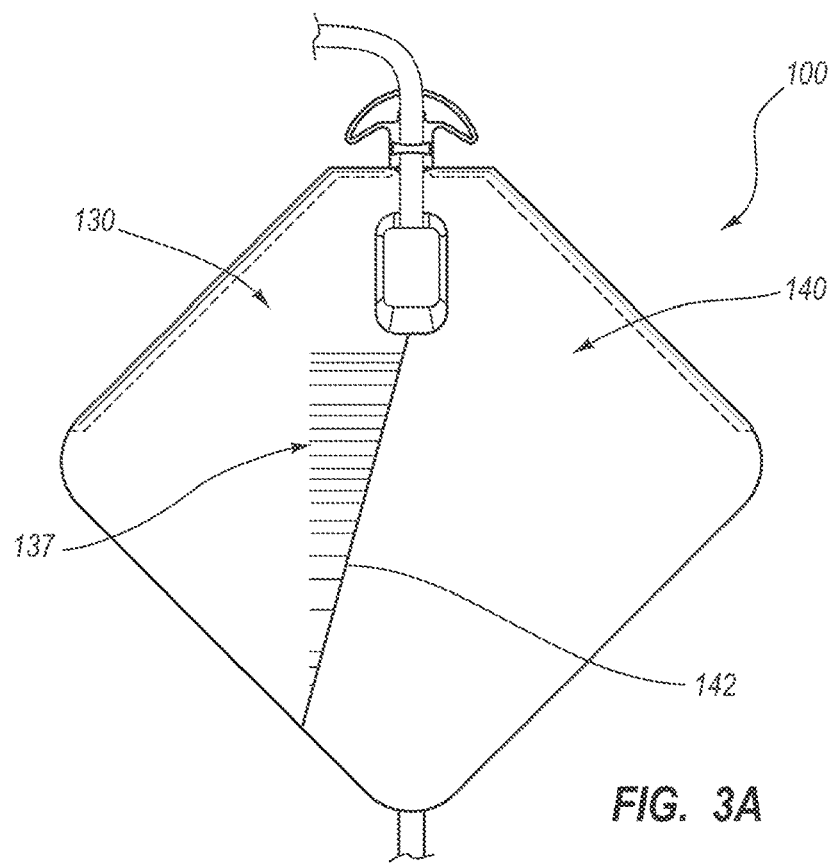
FIG. 3A is a front elevation view of the bodily fluid drainage assembly of FIG. 1 before the bodily fluid drainage assembly has received any fluid.
Figure 3B:
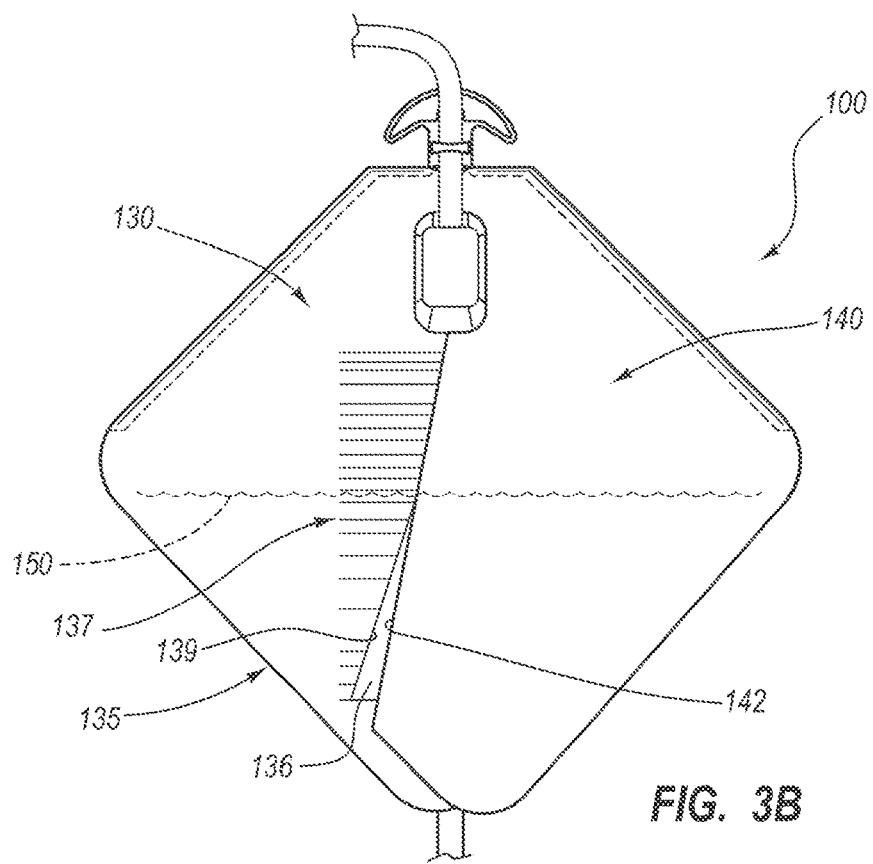
FIG. 3B is a front elevation view of the bodily fluid drainage assembly of FIG. 3A after the bodily fluid drainage assembly has received some fluid.
Figure 3C:
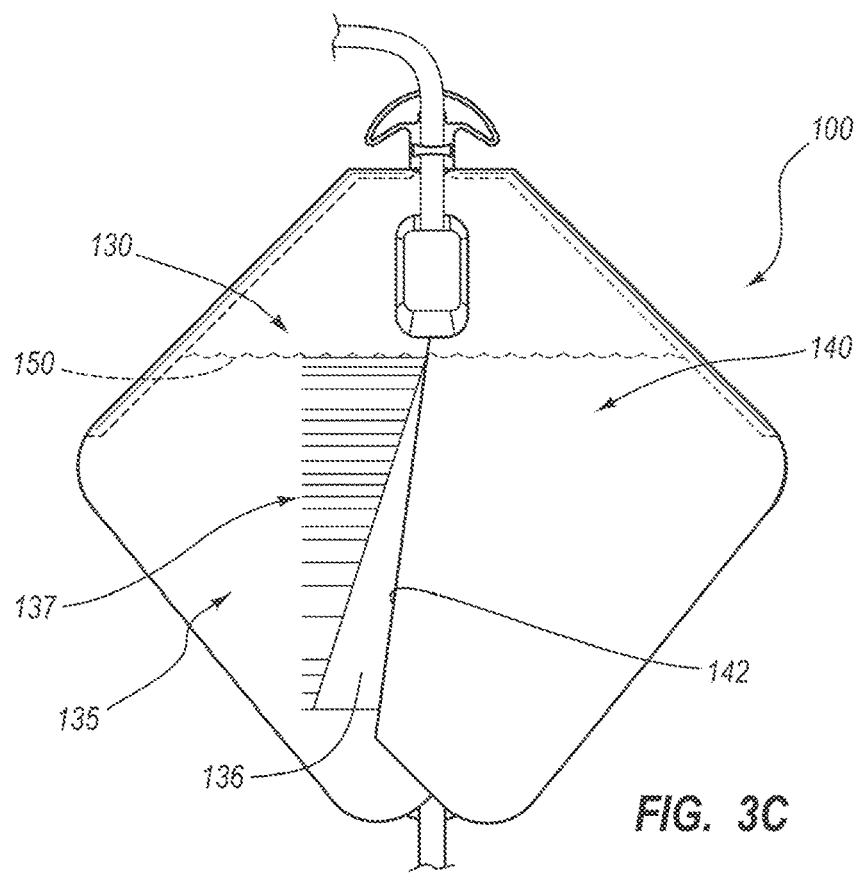
FIG. 3C is a front elevation view of the bodily fluid drainage assembly of FIG. 3A after the bodily fluid drainage assembly has received additional fluid.
Figure 3D:
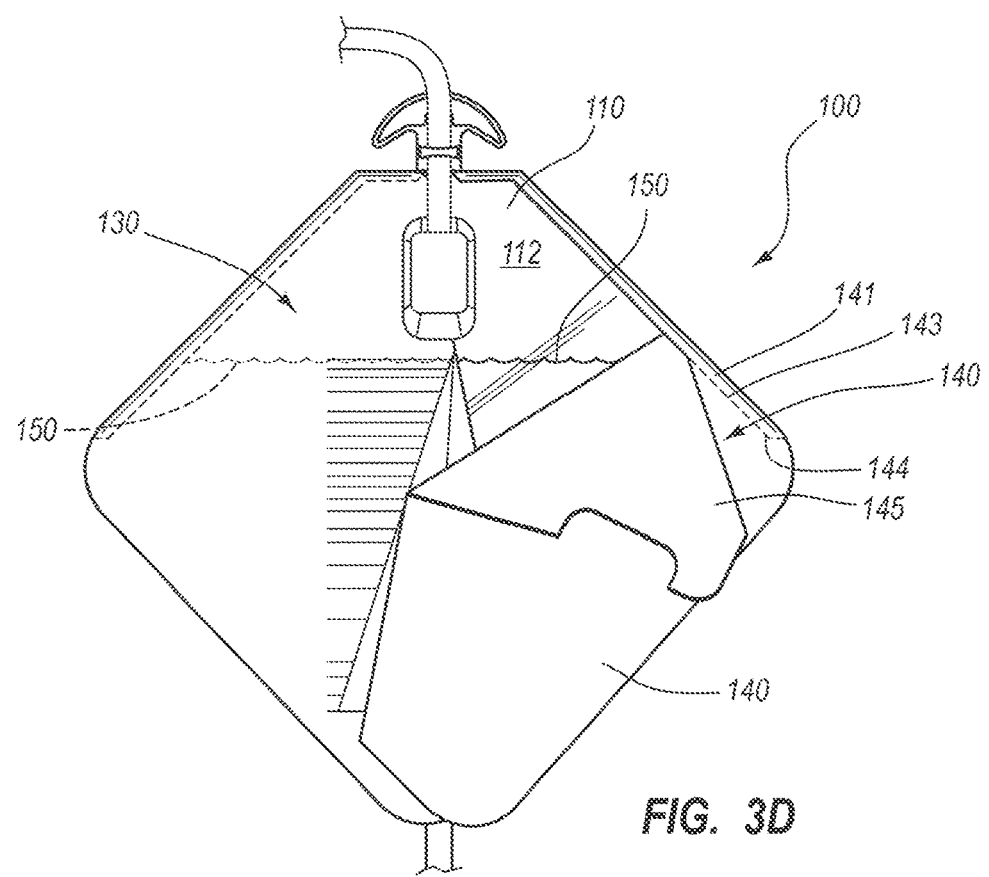
FIG. 3D is a front elevation view of the bodily fluid drainage assembly of FIG. 3A after a portion of the bodily fluid drainage assembly has been torn.

FIGS. 3A-3D depict bodily fluid drainage assembly 100 from a front elevation view, wherein in FIG. 3A, the assembly does not contain fluid; in FIG. 3B, the assembly has received some fluid; in FIG. 3C the assembly has received some additional fluid; and in FIG. 3D, the second cover of the assembly has been partially torn away. In the depiction of FIG. 3A bodily fluid drainage assembly is in an empty, planar (e.g., flat) configuration. In the illustrated arrangement, the first and second covers 130 and 140 hang downwardly so as to cover the front face of the fluid bag 110. As the covers 130, 140 are opaque, they obscure the contents of the fluid bag 110. Graduations 137 of the second volume indicator 135 are visible, but partially obscured by inner edge 142 of second cover 140.

When assembly 100 receives fluid 150, as depicted in FIG. 3B, the fluid bag 110 changes from an unexpanded (e.g., substantially planar) configuration to an increasingly expanded (e.g., more rounded or ovalized, in horizontal cross-section) configuration. As a result, the fluid bag 110 may expand more in a central region thereof than it does near the seam 113, which can cause the first cover 130 and second cover 140 slide over each other in opposing outward directions, such that the position of inner edge 142 of the second cover 140 is altered relative to the second volume indicator 135 of the first cover 130. In the depiction of FIG. 3B, the assembly 100 has received enough fluid that inner edge 142 has slid far enough that a portion of the fluid level indicator 136 has become visible. The approximate volume of the liquid may be determined by identifying among graduations 137 those that are adjacent to the uppermost portion of the fluid level indicator 136 that is visible before inner edge 142 obscures the fluid level indicator. As such, an approximate volume of a fluid within bodily fluid drainage assembly 100 may be ascertained without directly viewing the fluid within the fluid bag. In the illustrated embodiment, an approximate fluid volume reading can be obtained from the graduation 137 that is nearest to the intersection of the linear edge 139 of the fluid level indicator 136 and the inner edge 142 of the second cover 140.

In the depiction of FIG. 3C, assembly 100 has received additional fluid 150 such that inner edge 142 of second cover 140 has slid further over the first cover 130 and second volume indicator 135 in an outward direction. Inner edge 142 thus has revealed more of fluid level indicator 136, such that a new approximate volume is indicated by the fluid level indicator 136, graduations 137 and inside edge 142 of second cover 140 in a manner such as described above. As shown in FIG. 3C, inner edge 142 has slid across fluid level indicator 136 to reveal the indicator up to the approximate level of fluid 150.

FIG. 3D depicts assembly 100 as shown in FIG. 3D after a portion of second cover 140 has been removed. If a person would like to directly observe fluid 150 through front panel 112 of bag 110, second cover 140 may be partially or completely removed from assembly 100 via rupturing perforations 144. In the depiction of FIG. 3D, a portion of second cover 140 has been torn from assembly 100 to form a flap 145. Likewise, first cover 130 may be partially or completely removed such that the graduations 118 (see FIG. 1) located on front panel 112 may be used to estimate the volume of the fluid contained within bag 100. Fluid 150 may be temporarily visualized without removing first cover 130 and/or second cover 140 by lifting a bottom portion of the cover(s). As previously mentioned, in other embodiments, one or more of the covers 130, 140 may not include the rupturing perforations 134, 144, and may instead be removed, for example, along paths that border the seams 133, 143.

FIGS. 4A-4D depict another embodiment of a bodily fluid drainage assembly 200. Assembly 200 may be configured similarly and may function similarly as assembly 100, described herein in certain respects. Accordingly, like features may be designated with like reference numerals, with the leading digits incremented to "2." Relevant disclosure set forth above regarding similarly identified features thus may not be repeated hereafter. Moreover, specific features of the assembly 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the assembly 200. Any suitable combination of the features and variations of the same described with respect to the assembly 100 can be employed with the assembly 200, and vice versa. This method of disclosure also applies to the additional embodiments discussed further below.

Drainage assembly 200 may comprise a fluid bag 210, a first cover 230, a second cover 240, and a third cover 260. Fluid bag 210 may comprise an outer edge 211, a front face 212, a seam 213, an upper portion 215, a lower portion 216, a first volume indicator 217, an inlet tube 221, an outlet tube 222, and a hanger 224.

Fluid bag 210 may comprise one or more pieces of plastic material that are coupled together to form a bag that can retain fluid that has an outer edge 211 that defines a perimeter of the bag. Adjacent to the outer edge is a seam 213 that may be formed by coupling the one or more plastic pieces together via RF welding or any other suitable technique. In the depicted embodiment, an inlet tube 221 and hanger 224 are located on an upper portion 215 and an outlet tube 222 is located on a lower portion 216 of fluid bag 210. At least a portion of fluid bag 210 may be at least partially transparent; for example, at least a portion of front face 212 may be transparent, such that various characteristics of a fluid contained within the fluid bag may be determined. First volume indicator 217 may be printed, stamped, or otherwise marked on fluid bag 210. In the depicted embodiment, first volume indicator 217 comprises graduations that demark approximate volumes of a fluid contained within the fluid bag.

First cover 230 may comprise an opaque or at least partially opaque material that is coupled to fluid bag 210. First cover 230 may comprise an outer edge 231, an inner edge 232, a seam 233, perforations 234, and a second volume indicator 235. Second volume indicator may comprise a fluid level indicator 236 and graduations 237. Second cover 240 may comprise an outer edge 241, an inner edge 242, a seam 243 and perforations 244. Third cover 260 may comprise a window cover 261, a window 262, a cutout 263, perforations 264, and outer edges 265.

Figure 4A:
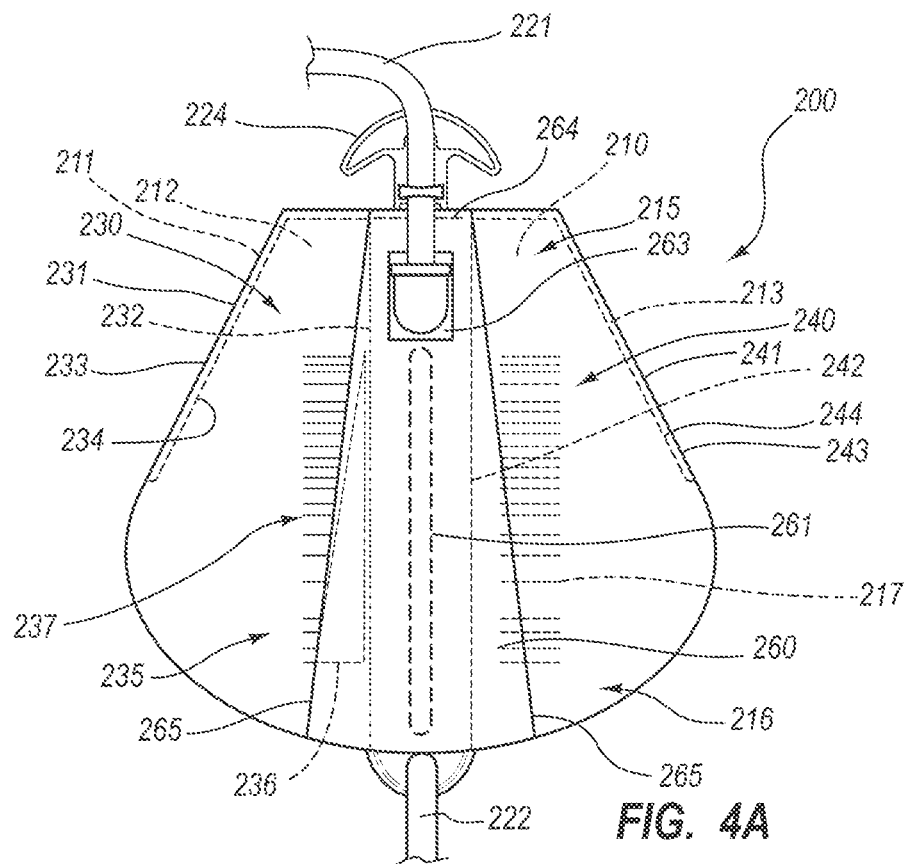
FIG. 4A is a front elevation view of another embodiment of a bodily fluid drainage assembly.
Figure 4B:
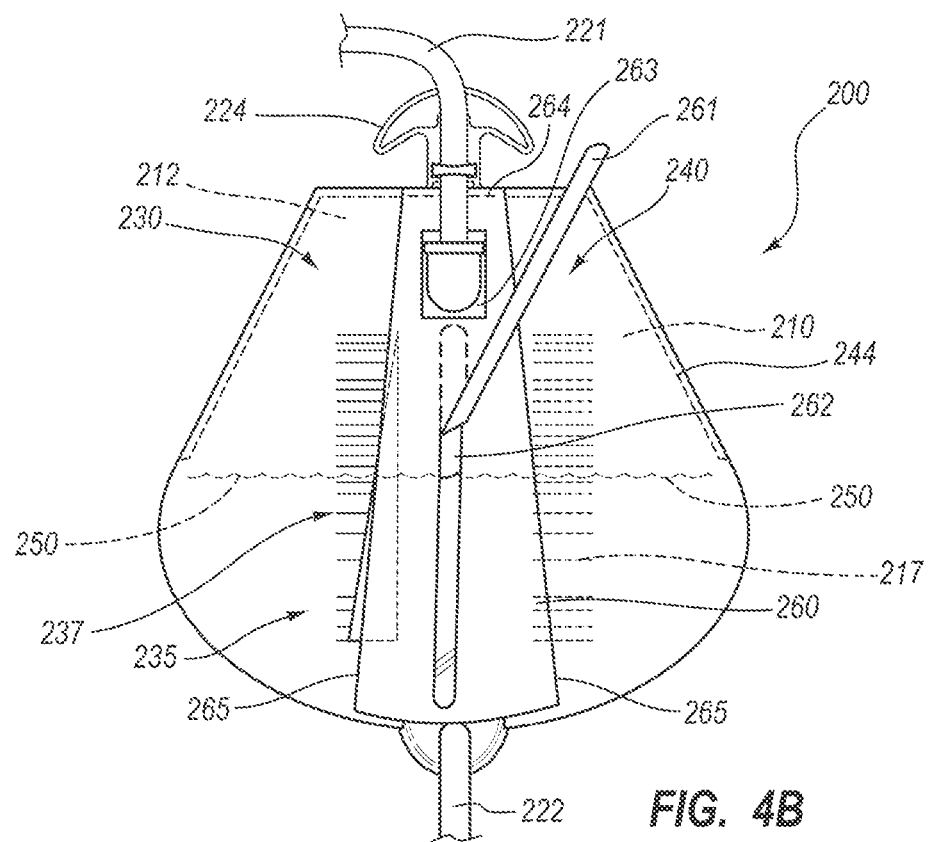
FIG. 4B is a front elevation view of the bodily fluid drainage assembly of FIG. 4A after the assembly has received some fluid.

FIG. 4B depicts bodily fluid bag assembly 200 after the assembly has received some fluid 250. Second volume indicator 235 may be configured to function similarly as second volume indicator 135, except that the first cover 230 cooperates with the third cover 230 in revealing the fluid level indicator 236. As assembly 200 receives fluid 250, fluid bag 210 may expand and cause the third cover 260 and first cover 230 to slide over each other such that fluid level indicator 236 becomes visible. A left outer edge 265 of the third cover 260 thus can operate in a manner similar to the inner edge 142 of the second cover 140 discussed above. The topmost visible portion of fluid level indicator 236 may correspond with a top level of fluid 250 such that an approximate volume can be determined by correlating the topmost visible portion of fluid level indicator 236 with the nearest graduation 237.

Figure 4C:
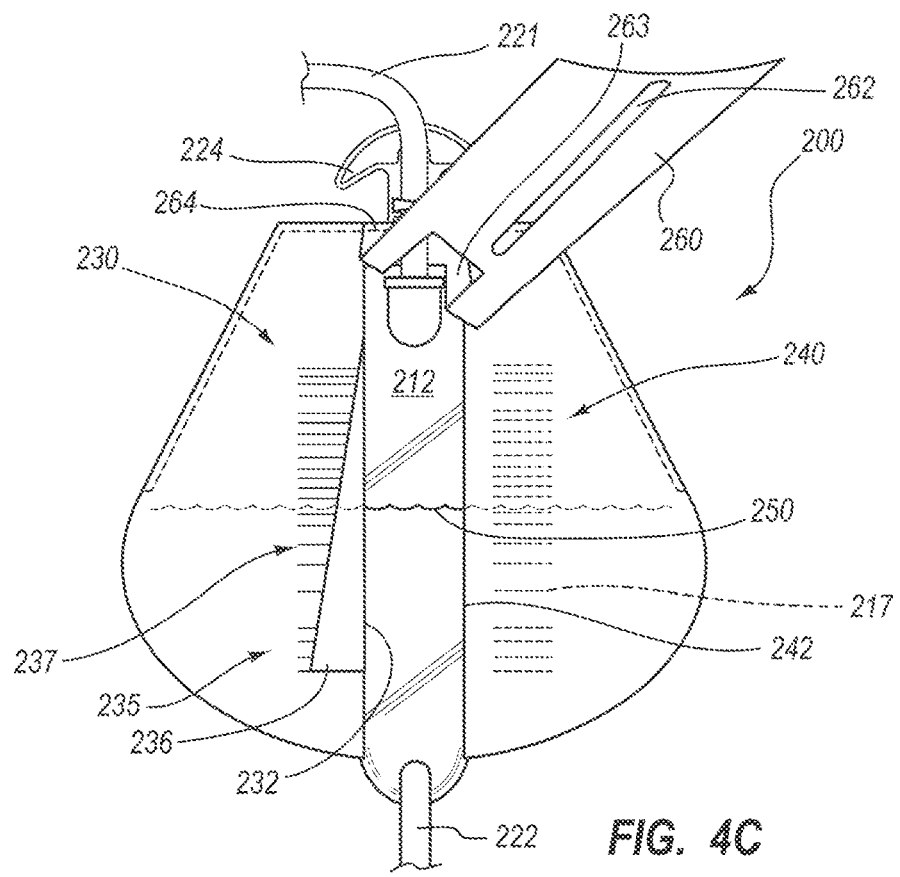
FIG. 4C is a front elevation view of the bodily fluid drainage assembly of FIG. 4B after a portion of the assembly has been torn.

As depicted in FIGS. 4B-4C, third cover 260 may comprise a window cover 261, a cutout 263, and perforations 264. Window cover 261 may comprise a removable opaque plastic that is the same material from which cover 260 is formed. When window cover 261 is removed, a portion of transparent window 262 is revealed such that a level of the fluid 250 can be determined. Window 262, when opened in this manner, thus may reveal a portion of the transparent or translucent front face 212 of fluid bag 210 that is positioned between, and not covered by, the opaque first and second covers 230 and 240. Accordingly, if desired, a practitioner can remove the window cover 261 so as to reveal a thin strip of the clear or semi-clear portion of the bag 210, and thereby provide another visual indicator of the fill level 250 of fluid within the bag 210. It is noted that the cutout 263 can be shaped and sized to accommodate the junction of the inlet tube 221 and the bag 210.

Figure 4D:
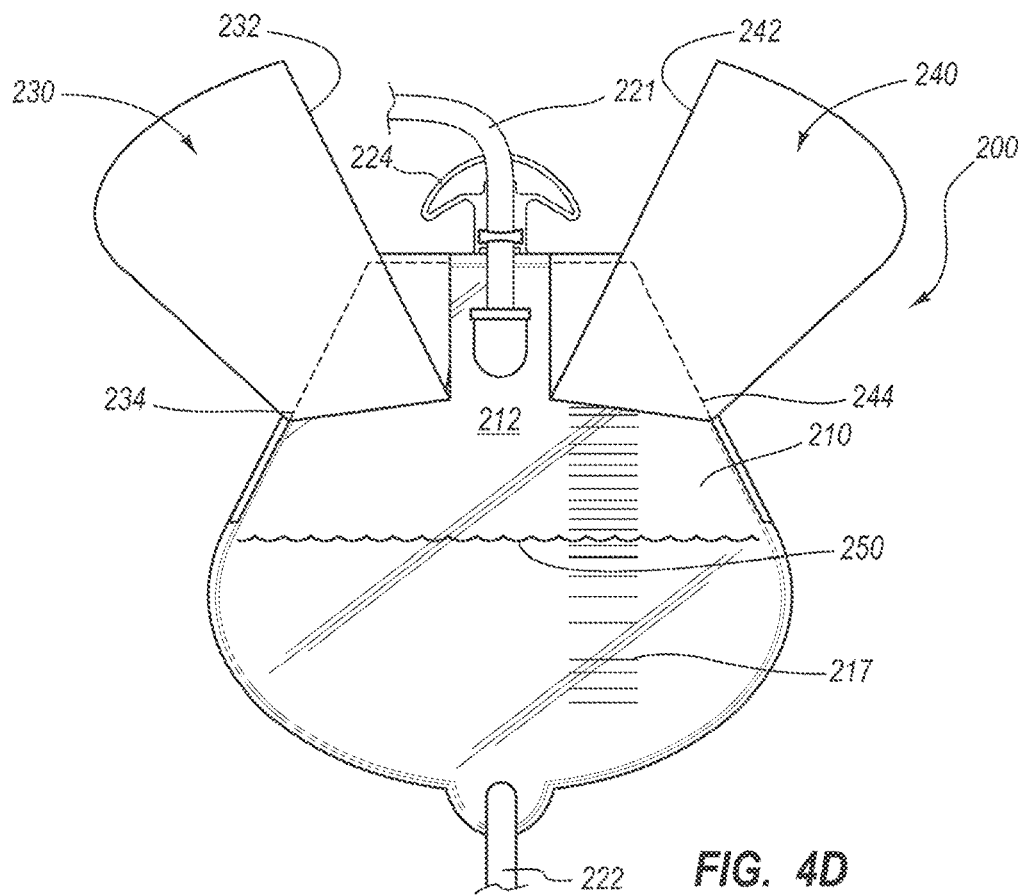
FIG. 4D is a front elevation view of the bodily fluid drainage assembly of FIG. 4C after a portion of the assembly has been removed.

FIG. 4D depicts bodily fluid drainage bag assembly 200 after third cover 260 has been removed and first and second covers have been partially removed. First volume indicator 217 may be used to find an approximate volume of fluid 250. For example, this determination can be achieved by temporarily lifting, or even by removing, second cover 240. First and second covers 230 and 240 may be removed by rupturing perforations 234 and 244 such that front face 212 is entirely revealed and at least the portion of fluid 250 nearest the front face 212 of the fluid bag can be visualized.

Figure 5A:
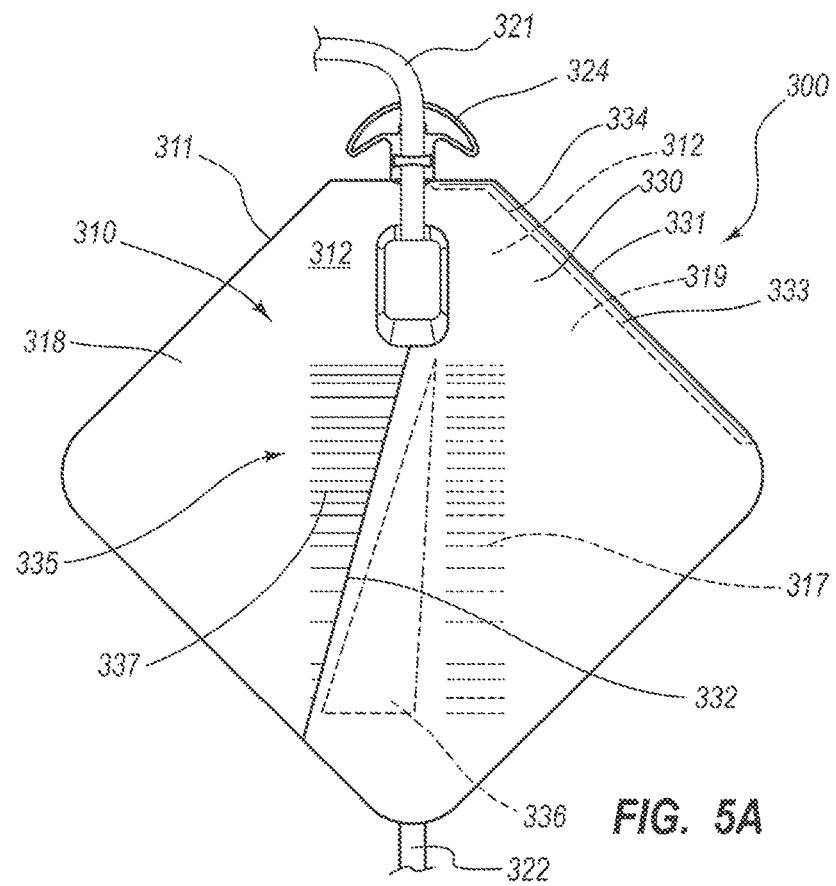
FIG. 5A is a front elevation view of another embodiment of a bodily fluid drainage assembly.
Figure 5B:
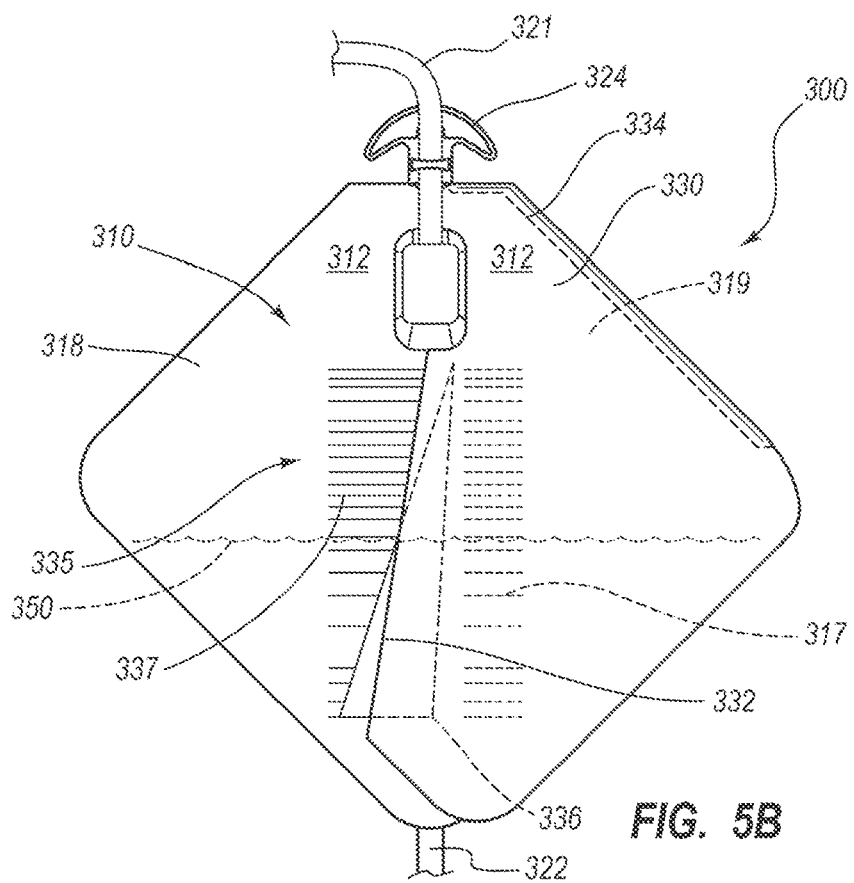
FIG. 5B is a front elevation view of the assembly of FIG. 5A after the assembly has received some fluid.
Figure 5C:
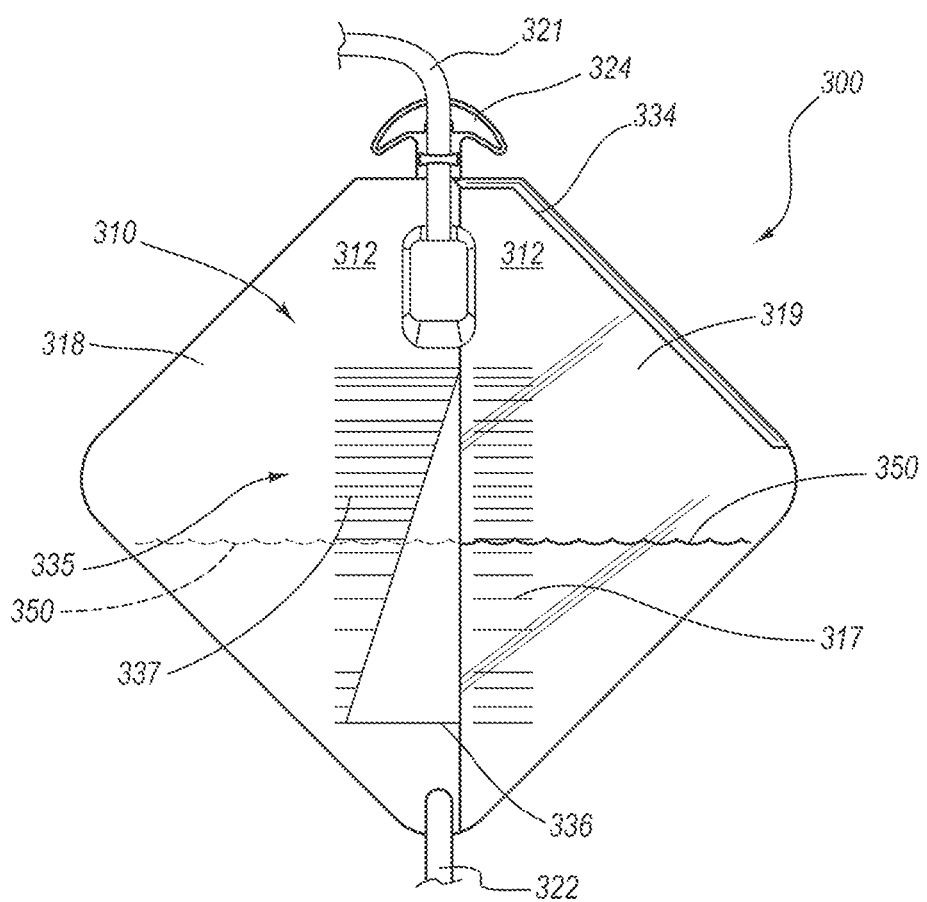
FIG. 5C is a front elevation view of the assembly of FIG. 5B after a portion of the assembly has been removed.

FIGS. 5A-5C depict another embodiment of a bodily fluid drainage bag 300 from front elevation views, wherein FIG. 53A depicts the assembly, FIG. 5B depicts the assembly after the assembly has received some fluid, and FIG. 5C depicts the assembly after a portion of the assembly has been removed. Assembly 300 may be configured similarly and may function similarly as assemblies 100 and/or 200 described herein. Assembly 300 may comprise a fluid bag 310, an inlet tube 321, an outlet tube 322, a hanger 324, and a cover 330.

Fluid bag 310 may comprise an outer edge 311, a front face 312, a first volume indicator 317, a left portion 318, and a right portion 319. Outer edge 311 may comprise a perimeter of fluid bag 310 and may at least partially comprise a seam formed by coupling one or more panels of plastic material together to form the fluid bag. Front face 312 may comprise an opaque left portion 318 and a transparent right portion 319. Left and right portions 318 and 319 are defined strictly for descriptive purposes and the portions themselves and features associated with them may be exchanged or flipped. Left and right portions may or may not define half or approximately half of fluid bag 310 front face 312.

Front face 312 of fluid bag 310 may comprise a transparent or translucent plastic material. Right portion 319 is at least partially transparent, except for first volume indicator 317, which may be printed on the right portion. First volume indicator 317 comprises graduations that allow for an approximate volume of a fluid within the bag. An opaque cover 330 is coupled to fluid bag 310 such that the transparent right portion 319 is obscured. Left portion 318 may be rendered opaque by printing, painting, or any other suitable technique and at least a portion of second volume indicator 335 may be printed on the left portion.

Cover 330 may comprise an outer edge 331, an inner edge 332, a seam 333, and perforations 334. Cover 330 comprises an opaque material that is coupled to fluid bag 310 to form seam 333, wherein outer edge 331 is at least partially aligned with a perimeter of the fluid bag. Perforations 334 may be formed in cover 330 such that the cover may be removed from assembly 300 to reveal right portion 319 and first volume indicator 317.

FIG. 5B depicts assembly 300 after the assembly has received a volume of fluid 350. Cover 330 is configured to slide over right portion 318 of bag 310 such that a portion of fluid level indicator 336 is revealed, wherein a topmost revealed portion of the fluid level indicator corresponds to the level of fluid 350. An approximate volume of fluid 350 may be ascertained by locating a graduation 337 that is adjacent to the topmost revealed portion of fluid level indicator 336. As such, an approximate volume of fluid 350 may be determined without directly viewing fluid 350.

FIG. 5C depicts assembly 300 after cover 330 has been removed such that transparent or translucent right portion 319 of front face 312 is visible. An approximate volume of fluid 350 can be determined by comparing the top of the fluid to the nearest graduation on first volume indicator 317. Graduations 337 of second volume indicator 335 may or may not report an accurate approximate volume, when compared directly to the top level of fluid 350.

Figure 6:
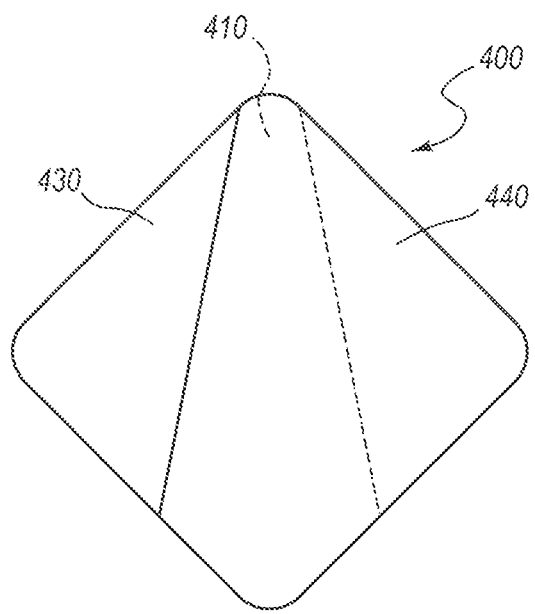
FIG. 6 is a front elevation view of another embodiment of a bodily fluid drainage assembly.
Figure 7:
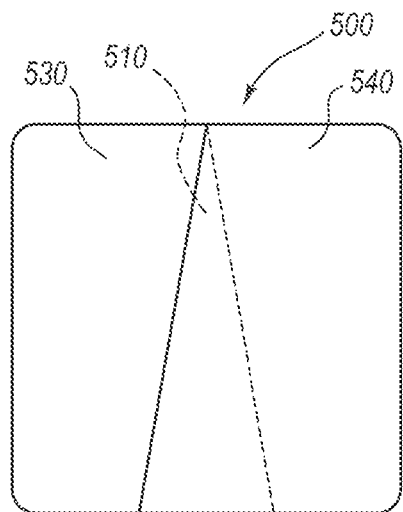
FIG. 7 is a front elevation view of another embodiment of a bodily fluid drainage assembly.
Figure 8:
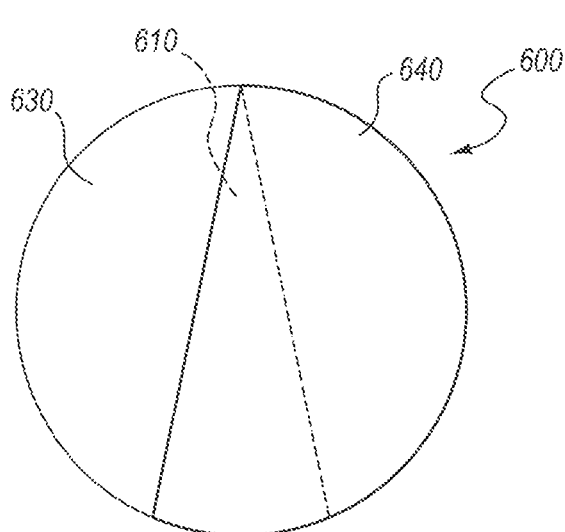
FIG. 8 is a front elevation view of another embodiment of a bodily fluid drainage assembly.
Figure 9:
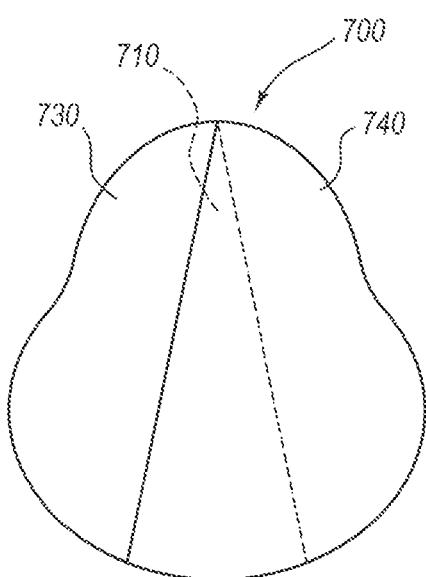
FIG. 9 is a front elevation view of another embodiment of a bodily fluid drainage assembly.

FIGS. 6-8 depict alternative embodiments of bodily fluid drainage assemblies from front elevation views, wherein FIG. 6 depicts assembly 400; FIG. 7 depicts assembly 500; FIG. 8 depicts assembly 600: and FIG. 9 depicts assembly 700. Assemblies 400, 500, 600, and 700 may be configured similarly and may function similarly as assemblies 100, 200, and/or 300 described herein. Assembly 400 may comprise a fluid bag 410, a first cover 430, and a second cover 440. Assembly 400 may further comprise an inlet tube, an outlet tube, and first and second volume indicators as described herein.

Likewise, assembly 500 may comprise a fluid bag 510, a first cover 530, and a second cover 540. Assembly 500 may further comprise an inlet tube, an outlet tube, and first and second volume indicators as described herein. Assembly 600 may comprise a fluid bag 610, a first cover 630, and a second cover 640. Assembly 600 may further comprise an inlet tube, an outlet tube, and first and second volume indicators as described herein. Assembly 700 may comprise a fluid bag 710, a first cover 730, and a second cover 740. Assembly 700 may further comprise an inlet tube, an outlet tube, and first and second volume indicators as described herein.

Figure 10:
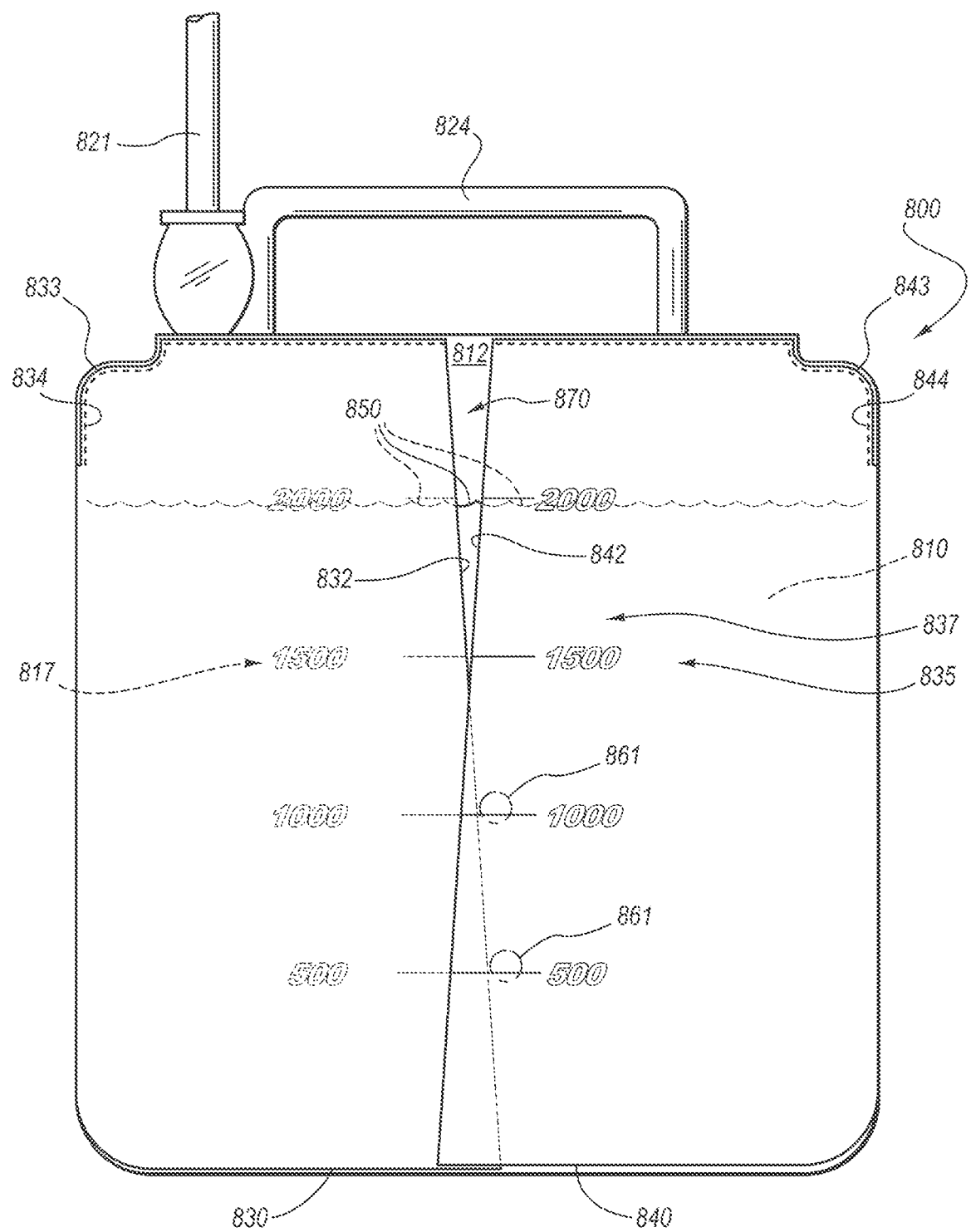
FIG. 10 is a front elevation view of another embodiment of a bodily fluid drainage assembly.
Figure 11:
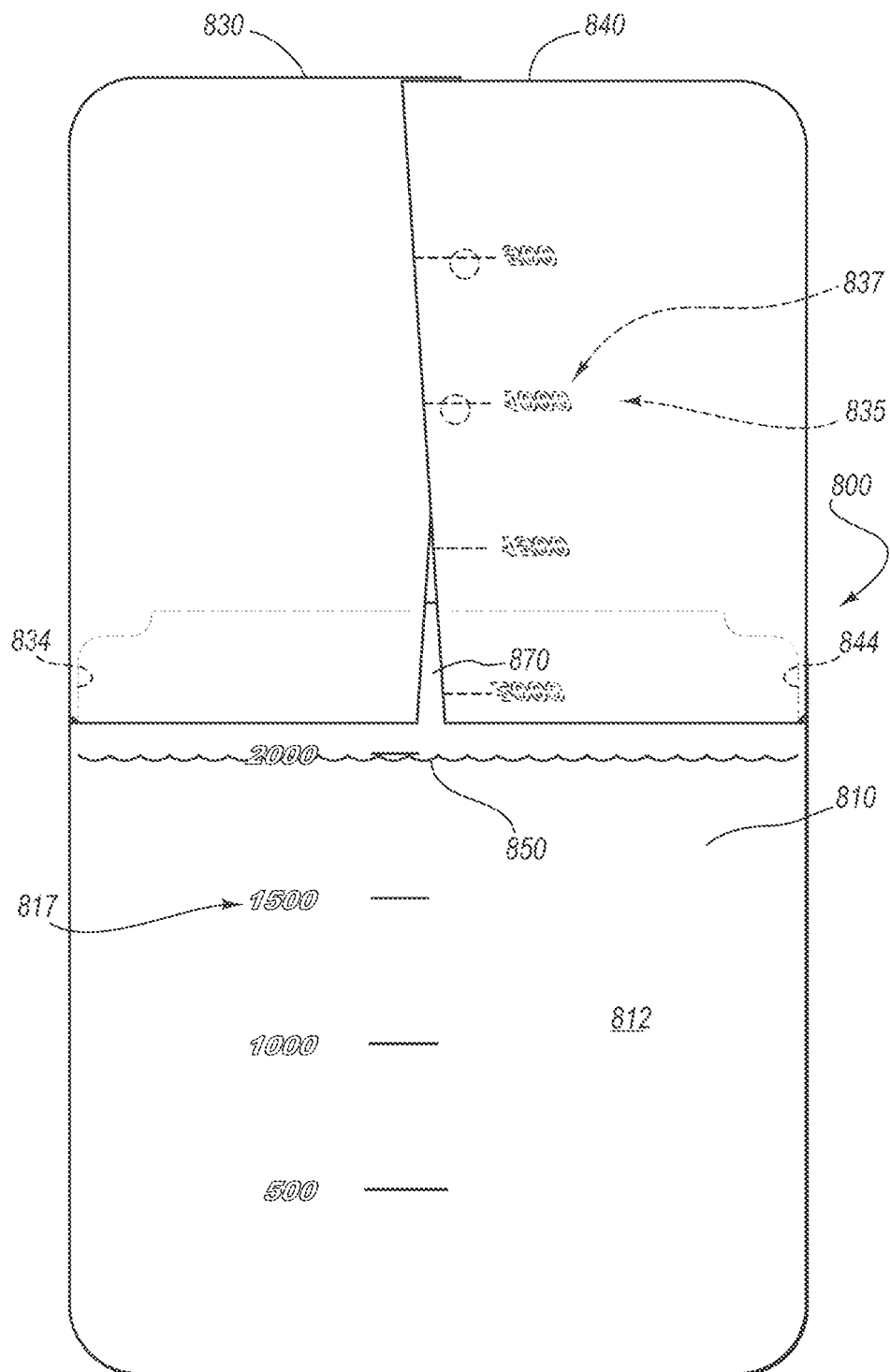
FIG. 11 is a front elevation view of the bodily fluid drainage assembly of FIG. 10 after fluid-obscuring flaps have been raised.

FIGS. 10-11 depict another embodiment of a bodily fluid drainage assembly 800 from a front elevation view. Assembly 800 may be configured similarly to and may function similarly as other bodily fluid drainage assemblies described herein. Assembly 800 may comprise a fluid bag 810, a first cover 830, and a second cover 840. Assembly 800 may further comprise an inlet tube 821, an outlet tube (not shown) and a hanger 824. The outlet tube may be configured similarly to outlet tube 122, described herein, except that in the depicted embodiment of assembly 800, the outlet tube is located on a rear face of fluid bag 810. In another embodiment, the outlet tube of assembly 800 is located on a front face of the fluid bag 810, and in yet another embodiment, the assembly does not comprise an outlet tube. Additionally, if an outlet tube is present on assembly 800, the outlet tube may comprise an outlet regulator, as is well known in the art.

Fluid bag 810 may comprise one or more pieces of material coupled together such that a front and a rear face are formed. Front face 812 and a rear face (not shown) may be coupled together at a seam that may be located adjacent to an outer edge of the fluid bag. A first volume indicator 817 may be located on a face of fluid bag 810 such that an approximate volume of a liquid 850 may be appreciated. In the depicted embodiment, first volume indicator 817 is located on front face 812.

One or more panels of material may be coupled to the fluid bag to obscure or at least partially obscure the contents of the fluid bag. First cover 830 and second cover 840 are two such panels, and may comprise opaque pieces of a plastic or fabric material. First and second covers 830 and 840 may be coupled to fluid bag 810 via seams 833 and 843. Perforations 834 and 844 may be formed in any portion of first and/or second cover 830 and 840 such that one or both of the covers can be removed from the fluid bag. In the depicted embodiment, perforations 833 and 843 are located adjacent to seams 834 and 844 such that if the covers are removed via the perforations, a majority of the covers are removed from the fluid bag.

The covers may function together to form a second volume indicator 835, which works similarly to those described herein, wherein the first and second covers 830, 840 slide over each other as the volume of the fluid in the fluid bag increases. An approximate volume may be appreciated by identifying the point at which the two covers overlap at their inside edges 832 and 842 and comparing that point to a scale 837, or second set of graduations, which can be located on one or more of the covers. In the depicted embodiment, the scale 837 is located on cover 840.

Removable portions 861 may comprise areas defined by perforations, wherein upon rupturing the perforations, a user may remove the removable portions thereby allowing direct visualization of a fluid within the fluid bag. When removed, removable portions may be said to form windows in the cover and each window may be formed in a predetermined location such that it may be used to appreciate a minimum volume of fluid in the fluid bag. As such, the removable portions 861 and/or the windows that are formable by removing the portions 861 may be said to define a third volume indicator.

In the depicted embodiment, the first cover is depicted as lying underneath the second cover; however, one skilled in the art will appreciate that the relationship may be reversed. Also, the removable windows are depicted as being on the second cover, whereas in other embodiments, the windows may be located on the first cover or on both covers.

A gap 870 is defined by inner edges 832 and 842 of the first and second covers 830 and 840 of material. Gap 870 is formed because the covers do not overlap along their entire length. Gap 870 may be employed as a fourth volume indicator, which may also be called a "gap volume indicator". If the volume of fluid is greater than, for example, about 1500 milliliters in the illustrated embodiment, then the second volume indicator may not continue to function; however, the fluid level will be visible within gap 870 (the fourth volume indicator) such that the fluid level can be compared to a scale printed on one of the covers. In this way, an approximate volume can be appreciated via gap 870 if the fluid volume is greater than a predetermined value. The volume at which second volume indicator 865 ceases to function and the fourth volume indicator begins to function may be any predetermined value.

FIG. 11 depicts assembly 800 from a front elevation view after first and second covers 830 and 840 have been lifted to reveal front face 812 of fluid bag 810, as well as first volume indicator 817, second volume indicator 835, and gap 870. Note that perforations 833 and 843 have not been ruptured and as such, the covers 830 and 840 have not been removed from the assembly; rather, the covers have been lifted. With the covers lifted, an approximate volume of fluid 850 may be appreciated via first volume indicator 817, which in this embodiment comprises a scale located on front face 812 of fluid bag 810.

Figure 12:
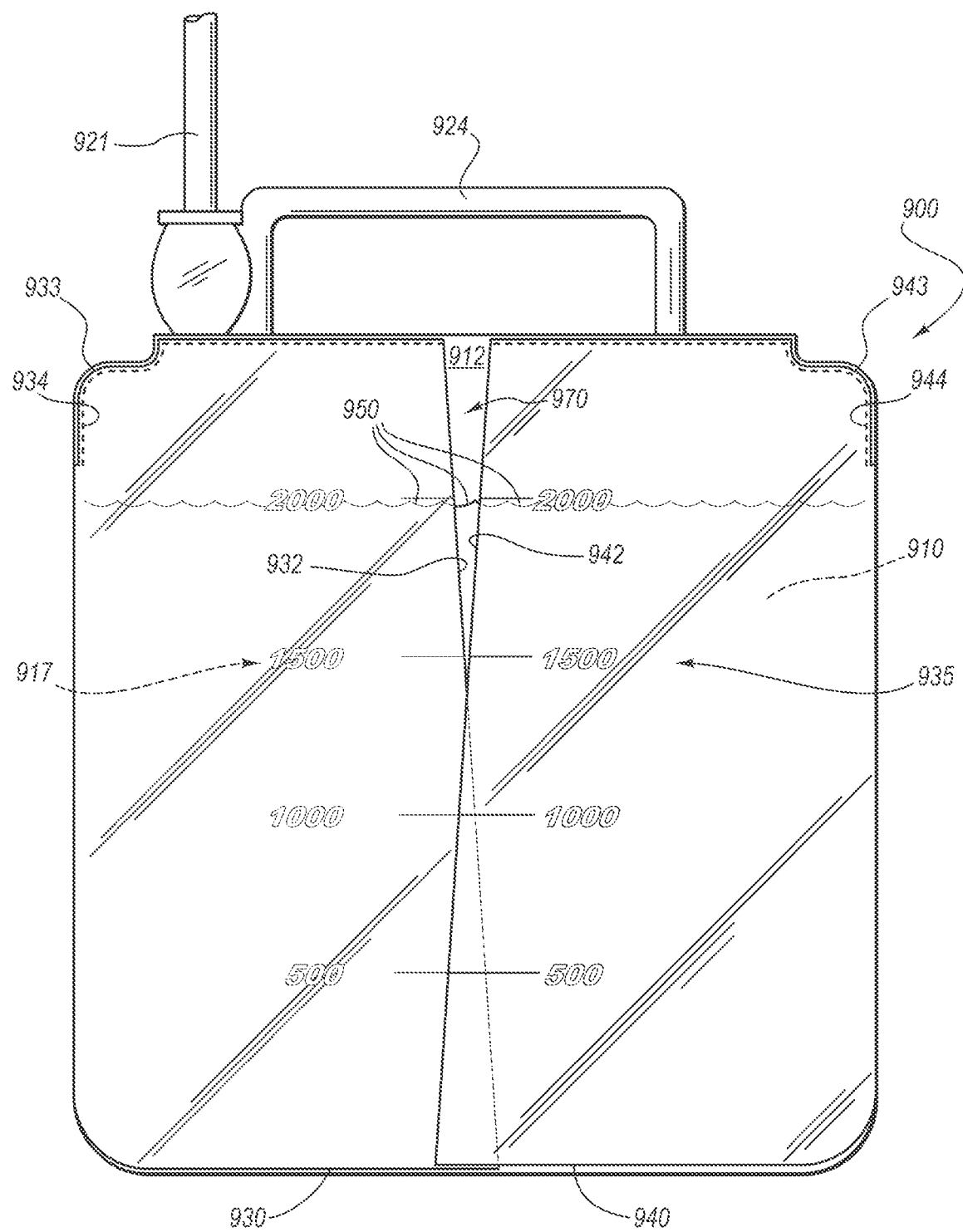
FIG. 12 is a front elevation view of another embodiment of a bodily fluid drainage assembly.

FIG. 12 depicts another embodiment of a bodily fluid drainage assembly 900 from a front elevation view. Assembly 900 may be configured similarly to and may function similarly as other bodily fluid drainage assemblies described herein. Assembly 900 may especially be similar to assembly 800, which is described herein. Assembly 900 may comprise a fluid bag 910 with a front face 912, a first cover 930 and a second cover 940. An inlet tube 921 and an outlet tube (not visible) may control fluid 950 inflow and outflow. A hanger 924 may be directly attached to fluid bag 910. Assembly 900 may comprise a first volume indicator 917, a second volume indicator 935, and a gap volume indicator 970. Gap 970 is defined by inner edges 932 and 942. The configurations and functions of these features have been described elsewhere herein.

First and second covers 930 and 940 may comprise a semitransparent or translucent plastic material, such as a clear material that is frosted. In another embodiment, the covers comprise a transparent material that has been colored as to render it semitransparent or transparent but wherein the fluid appears to have an altered color when viewed through one of the covers. In another embodiment, one of the covers is semitransparent and the other panel is opaque. As with other covers described herein, covers 930 and 940 may be removably coupled to fluid bag 910 at seams 933 and 943. In the depicted embodiment, covers 930 and 940 may be removed via the rupturing of perforations 934 and 944.

Figure 13:
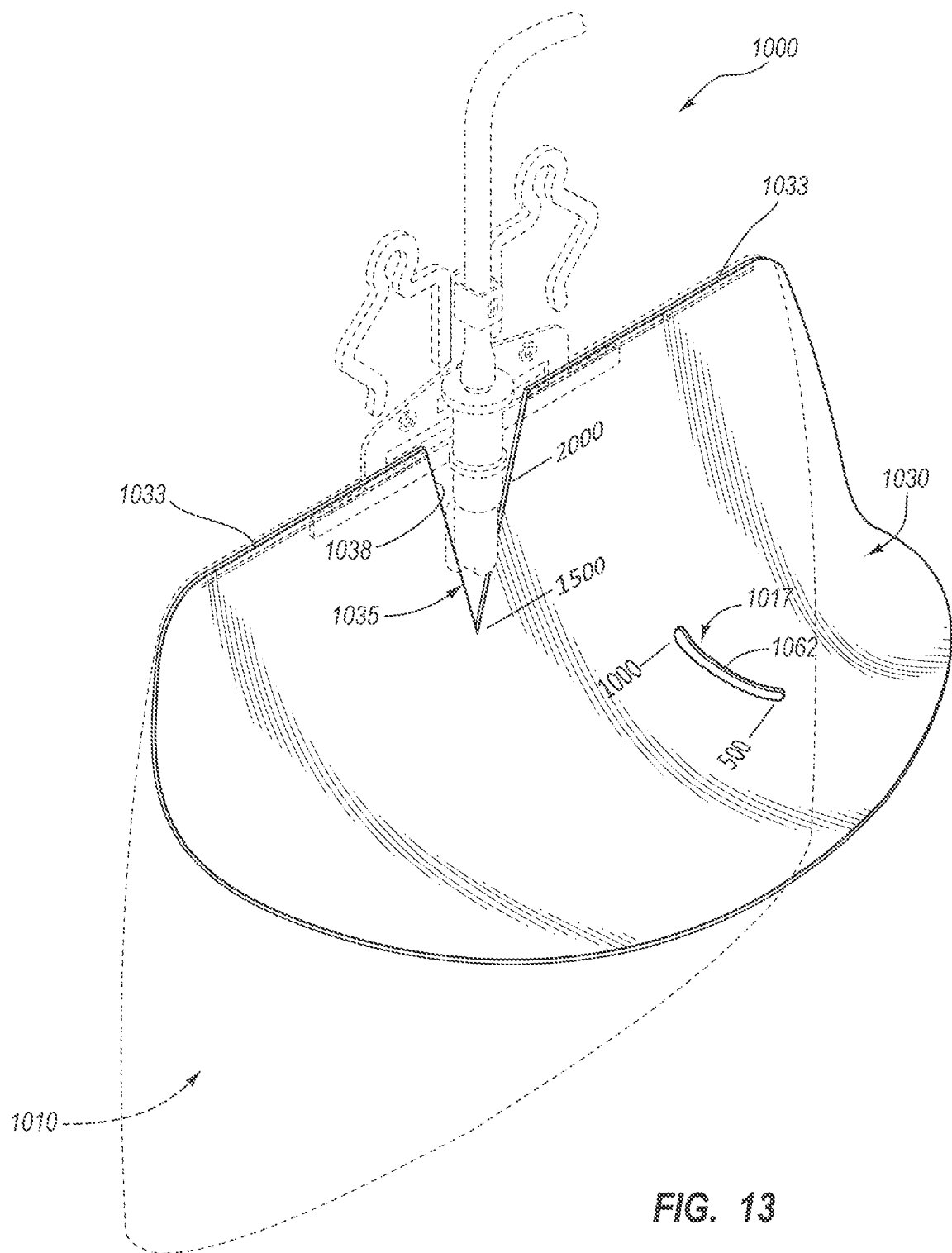
FIG. 13 is a perspective view of another embodiment of a bodily fluid drainage assembly, wherein a cover is partially lifted.

FIG. 13 is a perspective view of another embodiment of a bodily fluid drainage assembly 1000. Assembly 1000 may comprise a fluid bag 1010 and a cover 1030. Fluid bag 1010 may be configured similarly and may function similarly as other fluid bags described herein. For example, fluid bag 1010 may comprise an at least partially translucent material with volume markings indicated such that a fluid contained within the fluid bag may be visualized and an approximate volume estimated. Assembly 1000 may also comprise an inlet tube, outlet tube, outlet regulator, and/or a hanger, as described previously herein.

Cover 1030 may comprise a first volume indicator 1017 and a second volume indicator 1035. Cover 1030 may comprise a printed or opaque material, such as a plastic material, which obscures visualization of a fluid contained within fluid bag 1010. First volume indicator 1017 may comprise a window 1062 through which a fluid contained in fluid bag 1010 may be visualized. First volume indicator 1017 may also comprise graduations that indicate approximate volumes. Window 1062 may comprise a removable or cutout portion of cover 1030. If a meniscus or top level of a liquid contained within fluid bag 1010 is visible within window 1062, an approximate volume of the liquid can be ascertained by comparing the level of the fluid with an adjacent graduation. Window 1062 is depicted as being an elongated slot; however, those skilled in the art will recognize that the window may comprise any shape and its size can also vary.

Second volume indicator 1035 may comprise a cutout 1038 and graduations. Cutout 1038 may comprise a removable or cutout portion of cover 1030. If a level of a liquid contained within fluid bag 1010 is visible within cutout 1038, an approximate volume of the liquid can be ascertained by comparing the level with an adjacent graduation. Cutout 1035 is depicted as a "V" shape; however, those skilled in the art will recognize that the shape of the cutout may vary. Further, the size of the cutout may differ from the depiction.

Cover 1030 may be coupled to fluid bag 1010 at a seam 1033. Seam 1033 may be formed via RF welding, gluing, melting, stitching or any other suitable technique. Seam 1033 may include a weakened area that acts like a perforation, so that cover 1030 may be at least partially removable from fluid bag 1010, as described for other covers described herein. Seam 1033 may be formed on one or more sides of assembly 1000. In the depicted embodiment, seam 1033 is formed along a portion of a top side of fluid bag 1010 and cover 1030. As depicted in FIG. 13, if cover 1030 is not coupled to the fluid bag along one or more adjacent sides, the cover may be at least partially lifted such that the fluid bag can be directly viewed.

Figure 14:
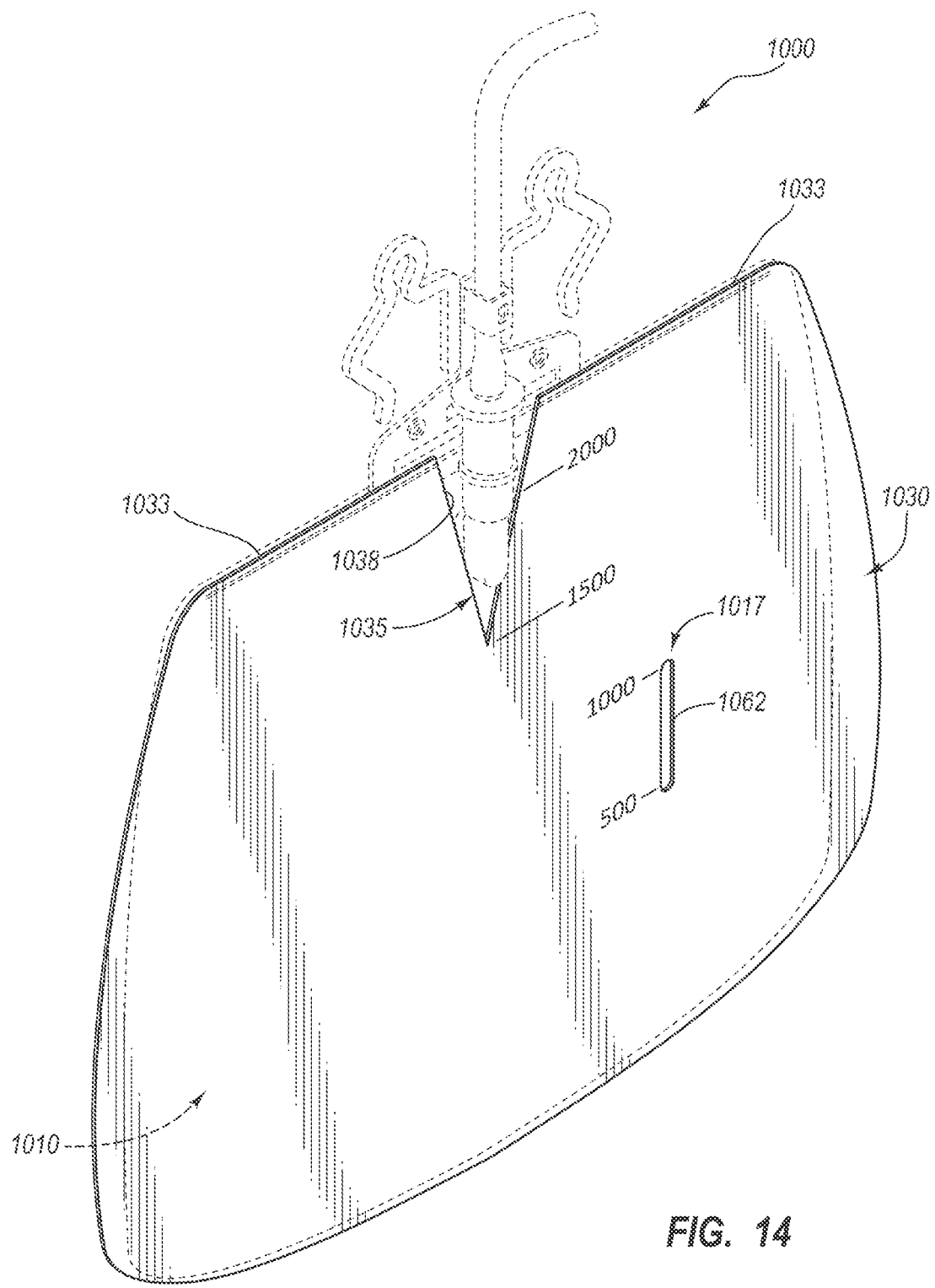
FIG. 14 is a perspective view of the bodily fluid drainage assembly of FIG. 13, wherein the cover is not lifted.

FIG. 14 is a perspective view of bodily fluid drainage assembly 1000, as depicted in FIG. 13, except that in the depiction of FIG. 14, cover 1030 is not lifted, or stated otherwise, is draped downward. As described above, assembly 1000 may comprise a fluid bag 1010, and a cover 1030. Cover 1030 is depicted as having a first and a second volume indicator 1017 and 1035. The first volume indicator may comprise a window 1062. Second volume indicator 1035 may comprise a cutout 1038. Each of the window 1062 and the cutout 1038 may be referred to as openings defined by the cover 1030.

Figure 15:
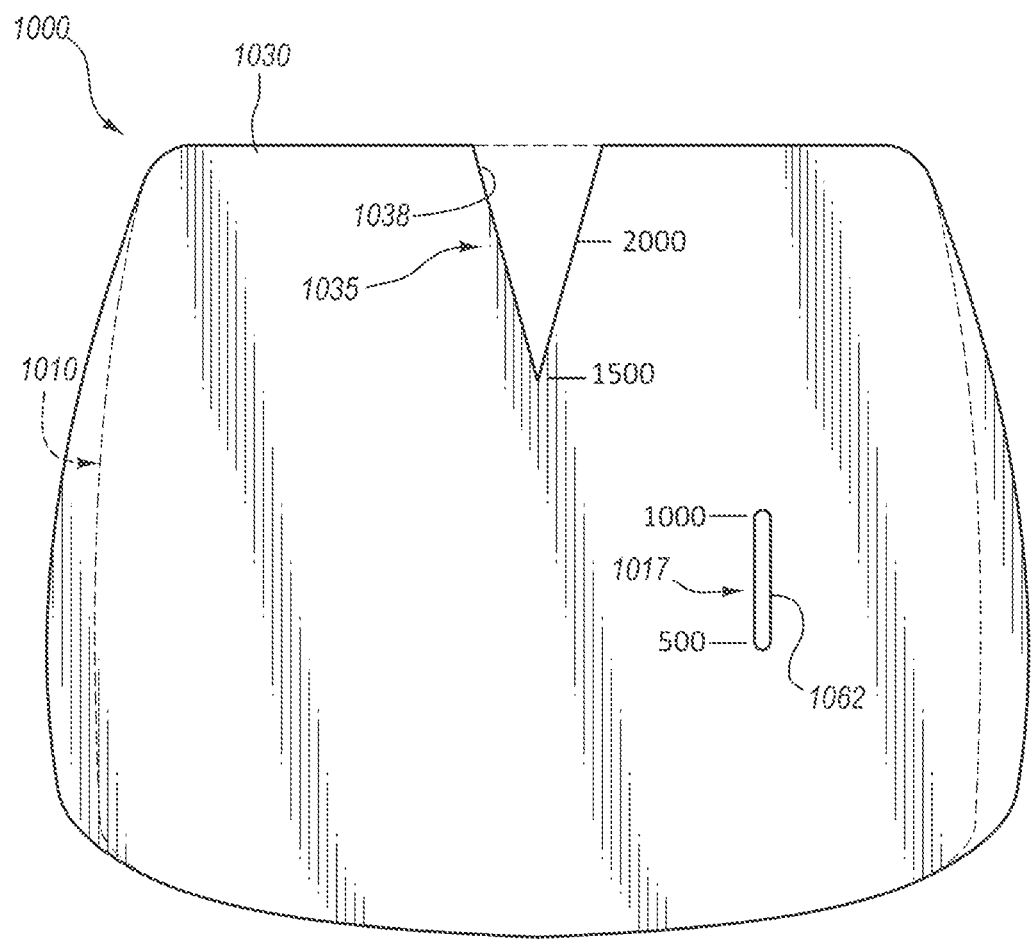
FIG. 15 is a front elevation view of the cover of the bodily fluid drainage assembly of FIG. 13.
Figure 16:
FIG. 16 is a side elevation view of the cover of the bodily fluid drainage assembly of FIG. 13.

FIGS. 15-16 depict cover 1030 of assembly 1000 from a front and side elevation view respectively. Cover 1030 comprises a first and second volume indicator 1017 and 1035. The first volume indicator may comprise a window 1062. Second volume indicator 1035 may comprise a cutout 1038. Cover 1030 is configured to cover fluid bag 1010. In the depicted embodiment, the cover overlaps the fluid bag on lateral sides and is approximately even with the fluid bag on the top and bottom sides. In another embodiment, the bottom of the cover that is opposite cutout 1038 extends beyond a bottom edge of the fluid bag. As depicted in FIG. 16, cover 16 may define a substantially planar shape. The 1030 cover can be flexible, pliable, compliant, or yielding so as to be readily moved from a generally planar shape to a curved shape for temporary viewing. Similarly, the cover 1030 may be able to curve somewhat about the fluid bag 1010 as the bag 1010 fills with fluid and becomes more rounded or ovoid (in horizontal cross-section).

Figure 17:
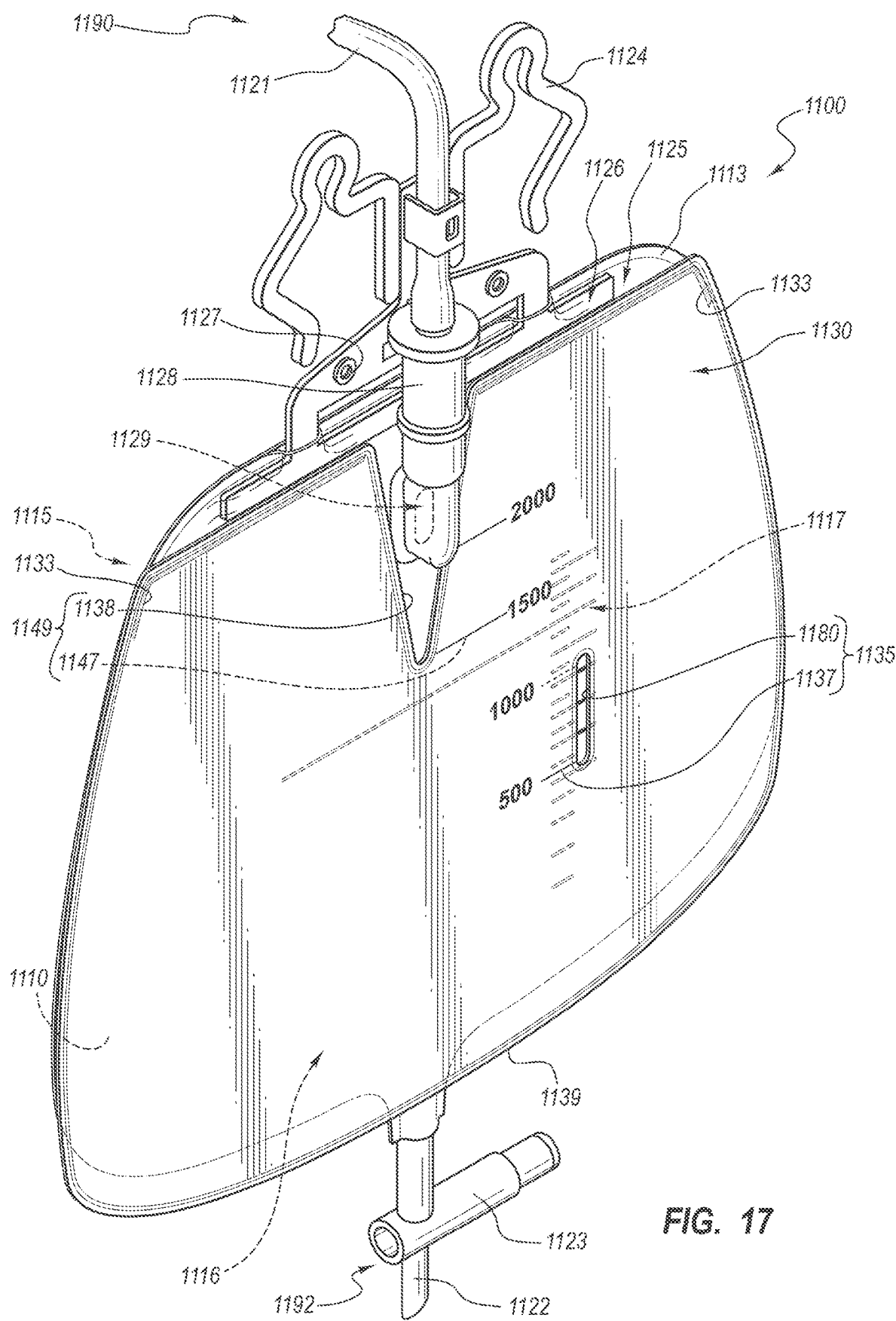
FIG. 17 is a perspective view of another embodiment of a bodily fluid drainage bag assembly with a fluid bag thereof in an empty or pre-use state and a cover thereof in an obscuring orientation.
Figure 18:
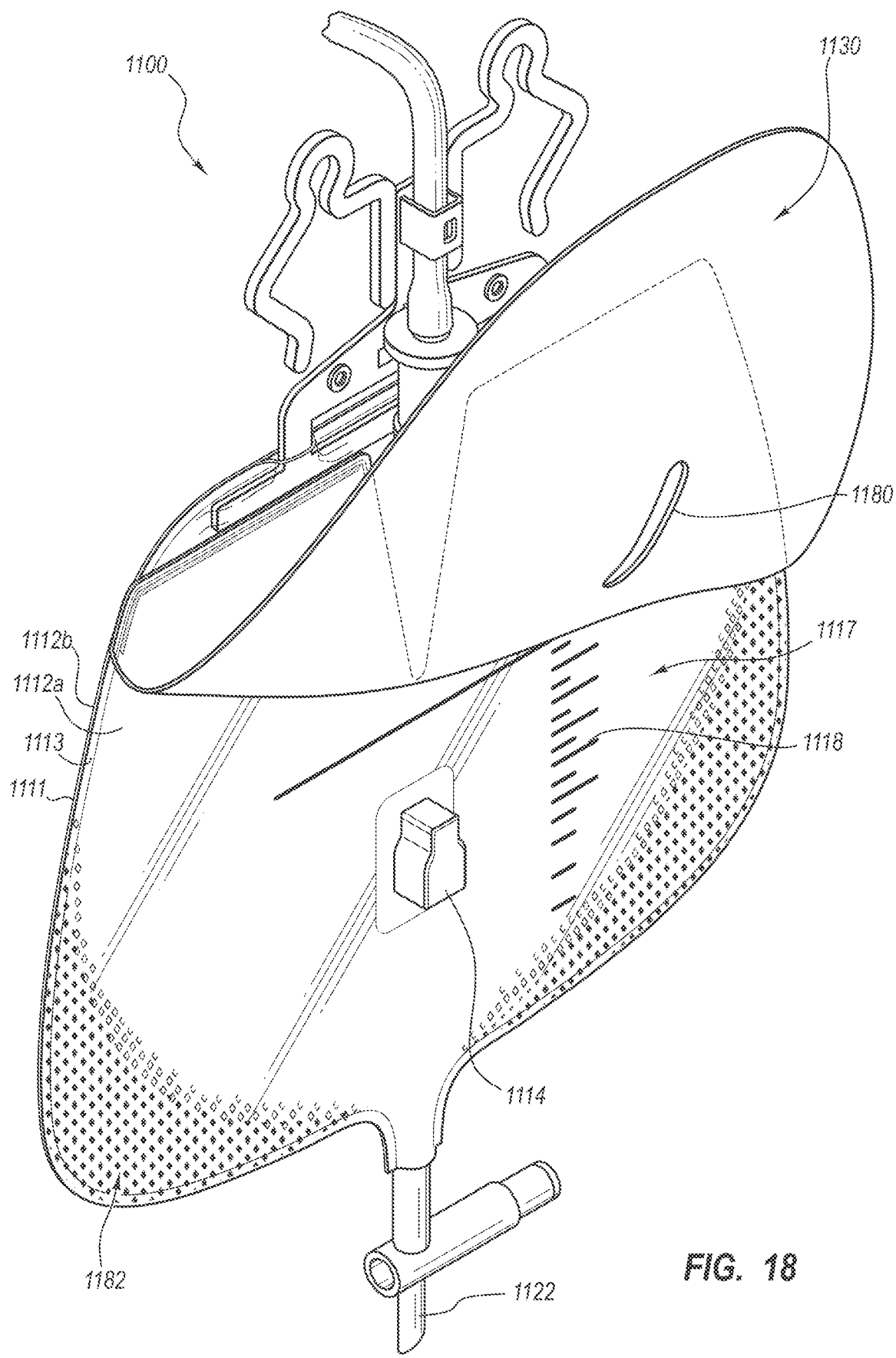
FIG. 18 is a perspective view of the bodily fluid drainage bag assembly of FIG. 17 with the fluid bag thereof in the pre-use state and the cover thereof in a viewing orientation.
Figure 19:
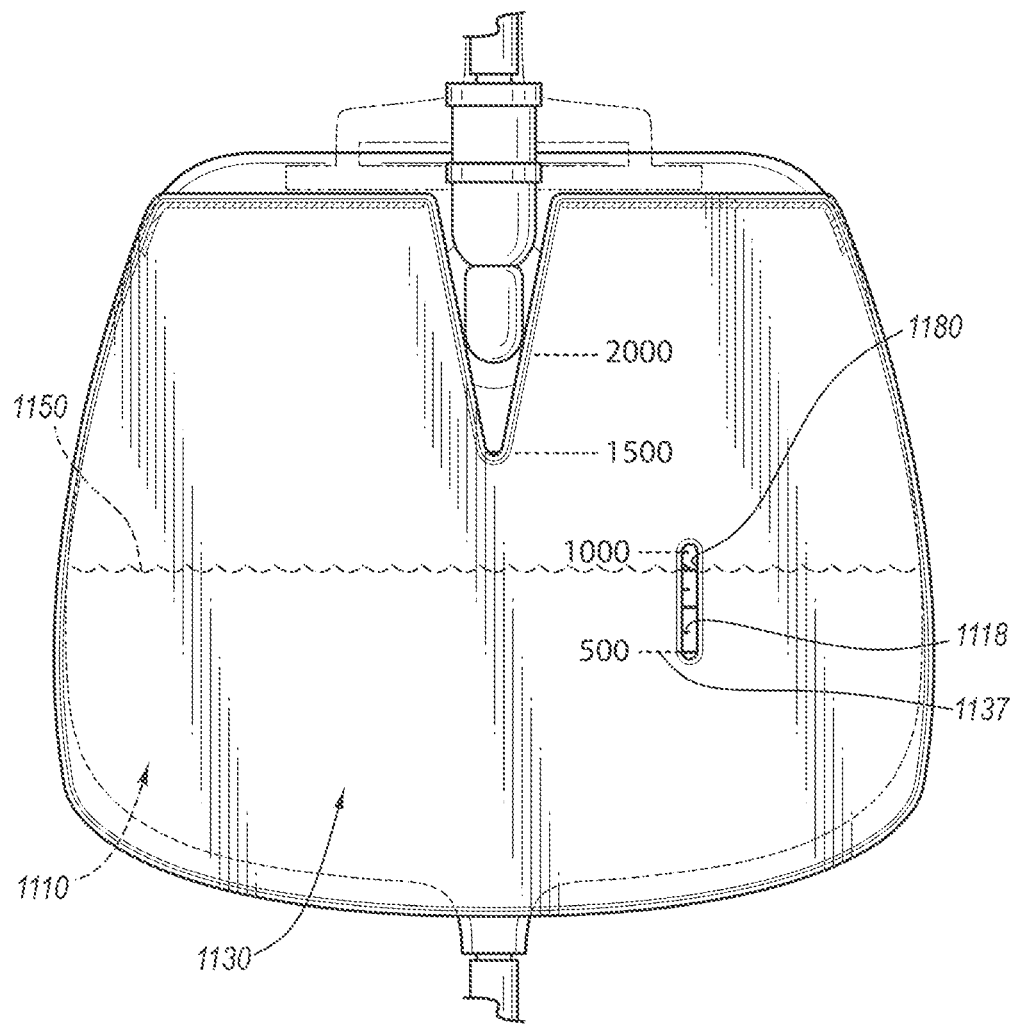
FIG. 19 is a front elevation view of the bodily fluid drainage bag assembly of FIG. 17 with the fluid bag thereof in a partially filled state and the cover thereof in the obscuring orientation.
Figure 20:
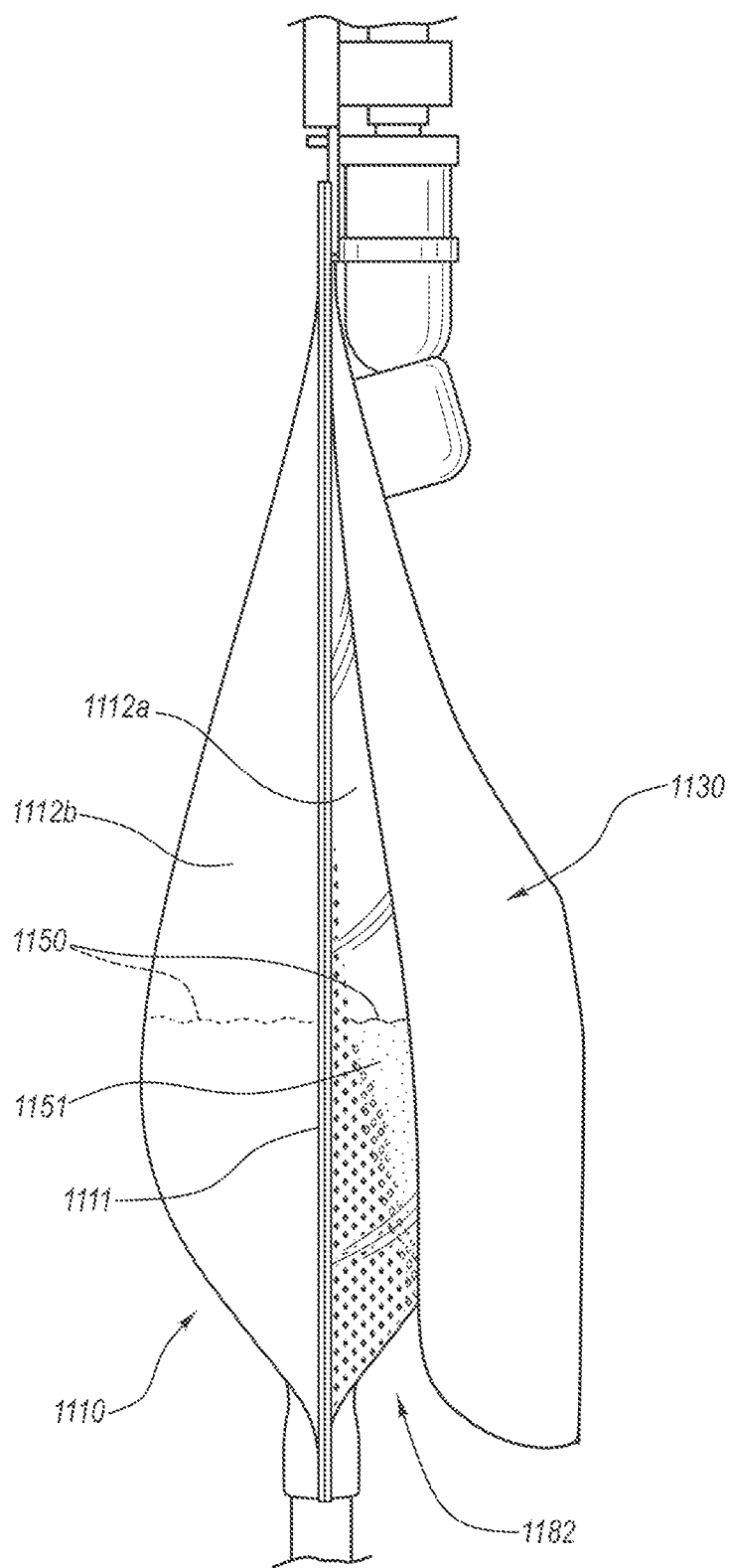
FIG. 20 is a side elevation view of the bodily fluid drainage bag assembly of FIG. 17 shown in the same operational state as that in FIG. 19.

FIGS. 17-20 depict another embodiment of a bodily fluid drainage assembly 1100 that resembles those discussed above in many respects, particularly the bodily fluid drainage assembly 1000. As previously indicated, appropriate portions of the foregoing discussion regarding other embodiments of bodily fluid drainage bag assemblies, their components, and their related methods are equally applicable to the assembly 1100, and vice versa. The assembly 1100 includes a fluid bag 1110 and a cover 1130. In FIGS. 17 and 18, the assembly 1100 is shown in a pre-use or unfilled state, in which the fluid bag 1110 is empty, void, or unfilled. In FIG. 17, the cover 1110 is shown in an obscuring (e.g., draped or lowered) orientation. In FIG. 18, the cover 1110 is shown in a viewing (e.g., raised) orientation. In FIGS. 19 and 20, the cover 1110 is shown in the obscuring orientation and the fluid bag 1110 is partially filled. The assembly 1110 is thus in a collection or filling state. These operational orientations of the assembly 1100 and its components are discussed further below.

The assembly 1100 is configured to receive a bodily fluid, optionally retain the fluid, and obscure the visibility of at least a portion of the fluid when it is within the fluid bag 1110. This can be desirable in a variety of settings. For example, in some embodiments, the fluid bag 1110 may be used to collect urine from a patient, and use of the cover 1130 to obscure a large portion of the collected urine can maintain the dignity of the patient. Moreover, an approximate volume of the bodily fluid that is within the fluid bag 1110 can be determined while the assembly 1100 is maintained in the obscuring orientation.

The fluid bag 1110 can be constructed in any suitable manner, such as those discussed above. With reference to FIGS. 17, 18, and 20, in the illustrated embodiment, the fluid bag 1110 includes a front panel 1112a of flexible material and a rear panel 1112b of flexible material. Any suitable material, may be used, such as a plastic (e.g., polyvinyl chloride, polyurethane, vinyl). The front and rear panels 1112a, 1112b are joined to each other so as to form a fluid-tight seal. For example, the panels 1112a, 1112b can be sealed to each other at or near an outer edge 1111 of the fluid bag 1110. The seal may be formed by one or more seams 1113 that extend about a periphery of the fluid bag 1110, which can be formed by RF welding, ultrasonic welding, heat sealing, or the like. In the illustrated embodiment, the rear panel 1112b is opaque and the front panel 1112a is transparent or semitransparent. As used herein, the term "semitransparent" is a broad term used in its ordinary sense and includes such properties as translucency. Accordingly, when the cover 1130 is raised (as in FIG. 18) such that the front panel 1112a is visible, the contents of the fluid bag 1110 can be readily discerned when the bag 1110 is viewed from a position in front of the assembly 1100. It is noted that a front face of the front panel 1112a and a rear face of the rear panel 1112b define an outer surface of the fluid bag 1110, and a rear face of the front panel 1112a and a front face of the rear panel 1112b define an inner surface of the fluid bag 1110. In the illustrated embodiment, a volume indicator 1117, which includes graduated volume markings or graduations 1118, is positioned on the front face of the front panel 1112a. For example, in the illustrated embodiment, the volume indicator 1117 is printed onto the front panel 1112a.

With reference to FIG. 17, a hanger 1124 can be attached to the fluid bag 1110 in any suitable manner. In the illustrated embodiment, a lower portion 1126 of the hanger 1124 is positioned within a non-fillable portion 1125 of the fluid bag 1110, which is formed by creating additional seams 1113 between the front and rear panels 1112a, 1112b. The hanger 1124 is thus permanently fixed to the bag 1110. In the illustrated embodiment, the hanger 1124 defines two apertures 1127 through which strings (not shown) may be threaded to assist in steadying the assembly 1100, or to be used as an alternative to the hooked portions of the hanger 1124 for attaching the assembly 1100 to a desired device (e.g., hospital bed or stand).

As with other assemblies described herein, the fluid bag 1110 can be coupled with an inlet fluid line 1190 through which a bodily fluid is received from a patient. In some embodiments, the fluid bag 1110 can further be coupled with an outlet fluid line 1192 through which fluid can be expelled from the fluid bag 1110. In the illustrated embodiment, the inlet fluid line 1190 is positioned at an upper end 1115 of the fluid bag 1110 and includes an inlet tube 1121 that is coupled with a valve assembly 1128, which can include a drip chamber and an anti-reflux valve. The valve assembly 1128 can deliver fluid into the fluid bag 1110 through an inlet opening 1129. The outlet fluid line 1192 is positioned at a lower end 1116 of the fluid bag 1110 and includes an outlet tube 1122, which may include an output regulator 1123. The fluid bag 1110 may further comprise an outlet tube holder 1114, such as a slot, loop, or hook that is configured to receive and reversibly retain outlet tube 1122 in an at least partially upright position, such as when the assembly 1100 is in a packaged or pre-use state.

The cover 1130 can include a volume indicator 1135 such as various volume indicators described above. The illustrated volume indicator 1135 includes a window 1180 and one or more graduations 1137. A variety of configurations for the window 1180 and the graduations 1137 are possible. For example, a variety of shapes are possible for the window 1180, and the number and arrangement of the graduations 1137 may be varied. In the illustrated embodiment, the window 1180 defines a permanent opening through the cover 1130 and is fully encompassed by solid or unbroken portions of the cover 1130. The window 1130 defines a small, vertically oriented longitudinal slot. Only a small portion of the front face of the fluid bag 1110 is visible through the window 1180 when the cover 1130 is in the obscuring orientation. An approximate volume level can be determined when a top level of the bodily fluid is visible through the window 1180, such as by comparing the level of the liquid to the graduations 1137. Due to the fixed relationship between the upper end of the cover 1130 and the fluid bag 1110, the graduations 1137 can provide an accurate assessment of the approximate liquid volume when the cover 1130 hangs downwardly.

In the illustrated embodiment, the window 1180 may be oriented such that a portion of the graduations 1118 that are on the fluid bag 1110 are visible through the window 1180 when the cover 1130 is in the obscuring orientation. In certain embodiments, the bag graduations 1118 may be offset relative to the cover graduations 1137 when the fluid bag 1110 is devoid of fluid. The offset can account for relative movement between the cover 1130 and the fluid bag 1110 as the bag fills with fluid. In particular, as shown in FIG. 20, the fluid bag 1110 can transition from a generally flat configuration to an outwardly expanded or bowed configuration as it fills with the bodily fluid 1151, and in some arrangements, the cover 1130 may not strictly match the contour of the bag 1110 as the bag expands. This relative shift in positions can cause the graduations 1180 of the volume indicator 1135 to come into greater alignment with the graduations 1118 of the volume indicator 1117.

In the illustrated embodiment, the cover 1130 includes an additional volume indicator 1149. The volume indicator 1149 includes a recess, such as a notch or cutout 1138, and a set of graduations 1147. A bottom end of the cutout 1138 is at a position that is horizontally offset and spaced vertically from an upper end of the window 1180. Due to the difference in vertical positions between the cutout 1138 and the window 1180, the top level 1150 of the bodily fluid 1151 can remain below the cutout 1138 at all times that the window 1180 is used in determining the approximate volume of the fluid 1151, and the top level 1150 of the bodily fluid 1151 can remain above the window 1180 at all times that the cutout 1138 is used in determining the approximate volume of the fluid 1151. Accordingly, due to the relative vertical positions of the cutout 1138 and the window 1180, determining that a top level of a fluid is viewable through one or the other of the cutout 1138 and the window 1180 can provide a quick and convenient visual indication of a general fill level of the fluid bag 1110, which may be on a rougher scale than that provided by the graduations 1137, 1118 (e.g., ½ full, ⅔ full, ¾ full, etc., rather than a specific number of milliliters).

Each of the window 1180 and the cutout 1138 may be referred to as an aperture or opening in the cover 1130 through which a portion of the front panel 1112a of the fluid bag 1110 may be directly viewed. The window 1180 and the cutout 1138 may be formed in any suitable manner, such as, for example, by stamping, cutting, or punching.

A comparison between the obscuring orientation shown in FIG. 17 and the viewing orientation shown in FIG. 18 demonstrates that a greater portion of the front panel 1112a of the fluid bag 1110 is directly viewable from vantage point, or viewing position, that is in front of the assembly 1100 when the cover 1130 is in the viewing orientation. Accordingly, a practitioner may at times wish to lift the cover 1130 to gain a better view of the bodily fluid 1151 that has been collected in the fluid bag 1110. The cover 1130 may be lifted only partially, as shown in FIG. 18, or may be lifted fully so as to expose an entirety of the front panel 1112a. Moreover, in some instances, a practitioner may desire to transition the assembly 1100 to an "exposed orientation" by completely removing the cover 1130.

It is noted that the term "obscuring orientation," when used with respect to the cover 1130, does not necessarily connote that an entirety of the front panel 1112a is obscured (e.g., blocked or guarded from view, rendered difficult to view, or provided with a significantly altered appearance) by the cover 1130. Indeed, as demonstrated by the embodiment depicted in FIG. 17, restricted portions of the front panel 1112a can be viewed, observed, or visualized through the window 1180 and the cutout 1138 when the cover 1130 is in the obscuring orientation.

The cover 1130 can be attached to the assembly 1100 in any suitable manner. In the illustrated embodiment, the cover 1130 is fixedly attached to the bag 1110 along two separate cover seams 1133, which extend along an upper edge of the cover 1130 and continue a short way down opposing side edges of the cover 1130. In some embodiments, the cover seams 1133 may be positioned directly on top of the bag seams 1113. In other embodiments, the cover seams 1133 may extend alongside or spaced from the bag seams 1113. For example, the cover seams 1133 may be positioned slightly above a bag seam 1113 (not shown) that defines an upper edge of the fillable void or chamber portion of the fluid bag 1110 such that the bag seams 1113 and cover seams 1133 are separate from each other. Such an arrangement may facilitate removal of the cover 1130 without disrupting the bag seams 1113. As previously discussed with respect to other embodiments, the cover seams 1133 may provide an area or region of weakness along which the cover 1130 may be readily removed from the assembly 1100, if desired. Other regions of weakness (e.g., perforations) may also be used.

In some methods of manufacturing the assembly 1100, the bag seams 1113 may be formed at a different time from (e.g., before) formation of the cover seams 1133. In other embodiments, the seams 1113, 1133 may be formed simultaneously.

The cover 1130 may be said to be integral with the assembly 1100. For example, in some embodiments, the assembly 1100 is sterilized and packaged with all of the components shown in FIG. 17. While it may be possible to remove the cover 1130 from the assembly 1100, as just discussed, the cover 1130 is nevertheless a fixed and permanent component of the assembly 1100. For example, in the illustrated embodiment, if the cover 1130 is removed by pealing it along its region of weakness, a portion of the cover 1130 (generally the portion that is attached to the front panel 1112a by the cover seam 1133) nevertheless remains attached to the fluid bag 1110. In other embodiments, the cover 1130 can be selectively attachable to and detachable from the assembly 1100, such as with snaps, hook-and-loop fasteners, adhesives, or any other suitable temporary fastening system. For example, the fasteners can be positioned along an upper edge of the cover 1130 (e.g., at one or more positions along the path defined by the seam 1133 in the illustrated embodiment).

As previously mentioned, the cover 1130 is attached to the assembly at an upper end of the assembly 1100. In particular, the cover 1130 is attached to the upper end of the bag 1110. The cover 1130 thus naturally hangs or drapes downward so as to be positioned in front of the front face of the front panel 1112a. The cover 1130 thus conceals or obscures viewing of a large portion of the front panel 1112a, where the assembly is viewed from a position in front of the assembly 1100. In other embodiments, the cover 1130 may be attached to portions of the hanger 1124 and extend downwardly therefrom. In still other embodiments, the cover 1130 may by attached at other sides of the fluid bag 1110. For example, in some embodiments, a lower end of the cover 1130 may be attached at a bottom end of the fluid bag 1110 and an upper end of the cover 1130 may be selectively attached and detached from the assembly 1100 at or near the upper end 1115 of the fluid bag 1110. Such selective attachment and detachment may be achieved in any suitable manner, such as via snaps, hook-and-loop fasteners, adhesives, or other suitable fastening system.

With reference to FIGS. 18 and 20, the transparent or semitransparent front panel 1112a can further include an obscuring pattern 1182, which may be positioned in at least the bottom corners of the front panel 1112a. As shown in FIG. 20, the obscuring pattern 1182 can obscure at least a portion of the bodily fluid 1151 when the assembly 1100 is viewed from a vantage point at a side thereof.

By way of further explanation, in the illustrated embodiment, the cover 1130 is formed of a flexible material. When the assembly 1100 is in the unfilled state (e.g., FIGS. 17 and 18), the fluid bag 1100 can be substantially planar or flat, and the cover 1130 can hang substantially vertically and may likewise be substantially planar or flat. The cover 1130 may be positioned exclusively forward of the front panel 1112a, and it may obscure an entirety of the front panel 1112a (except for those portions that are visible through the window 1180 and the cutout 1138) from all or nearly all vantage points that are forward of the assembly 1100. Moreover, when the assembly is viewed directly from the side at a position where the cover 1130 may not obscure the front panel 1112a, the outer edge 1111 of the bag 1110 is the primarily visible portion thereof. And since the fluid bag 1110 is void in this orientation, there is nothing to conceal in any event.

However, as the fluid bag 1110 collects increasing amounts of bodily fluid 1151, the cover 1130 can be displaced forwardly and may not wrap around the outer sides of the fluid bag 1110, and thus may not conceal the contents of the bag from a side view (see FIG. 20). The obscuring pattern 1182 can aid in concealing the bodily fluid 1151 from such side vantage points.

Any suitable patterns or shapes may be used for the obscuring pattern 1182. In the illustrated embodiment, the obscuring pattern 1182 defines a gradient such that it is darker and opaque at the edges and becomes lighter and translucent at an interior edge thereof. The obscuring pattern 1182 may be printed on the bag 1180 (e.g. silkscreened) or attached thereto in any suitable manner.

Figure 21:
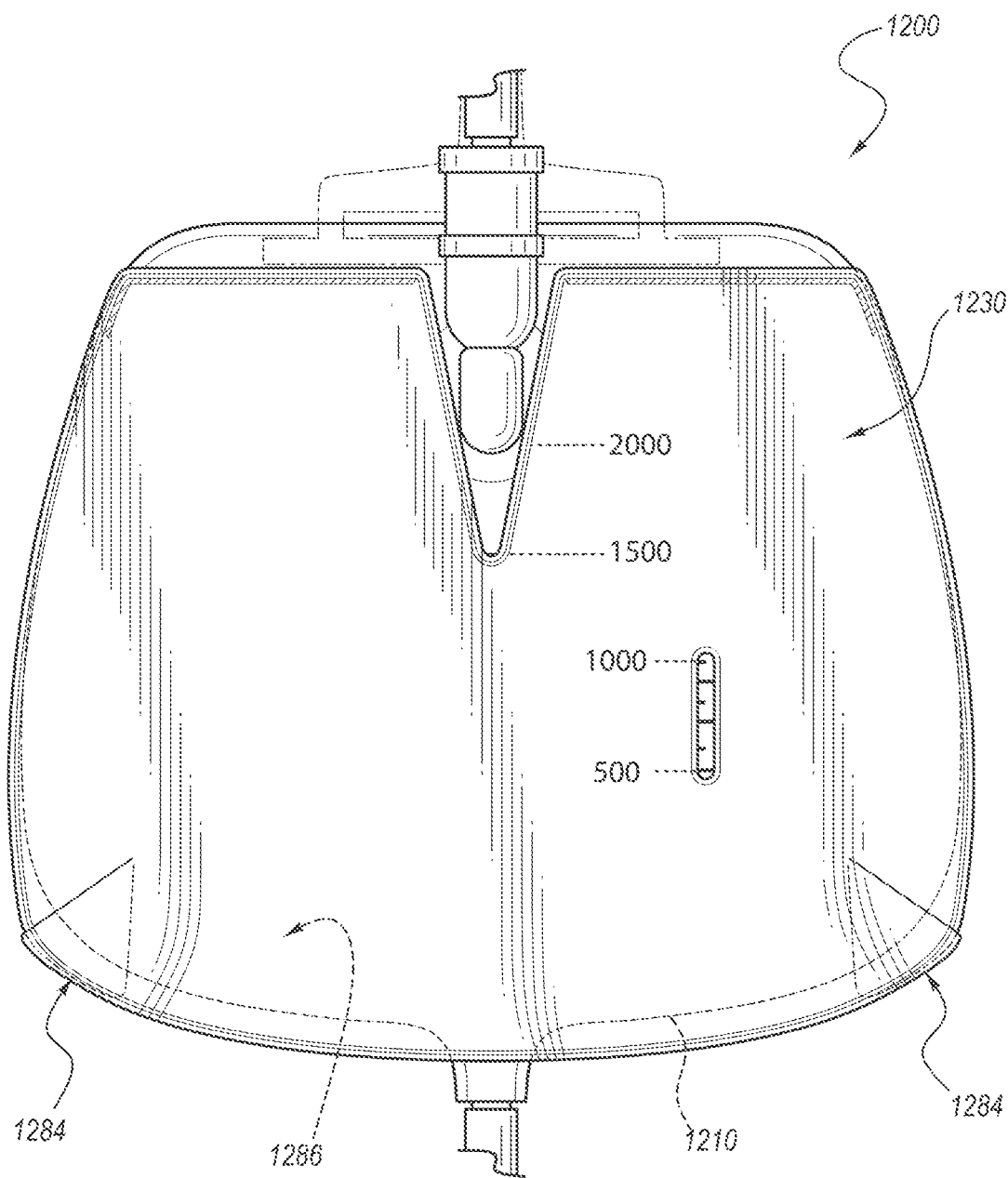
FIG. 21 is a front elevation view of another embodiment of a bodily fluid drainage bag assembly that includes a pleated cover.
Figure 22:
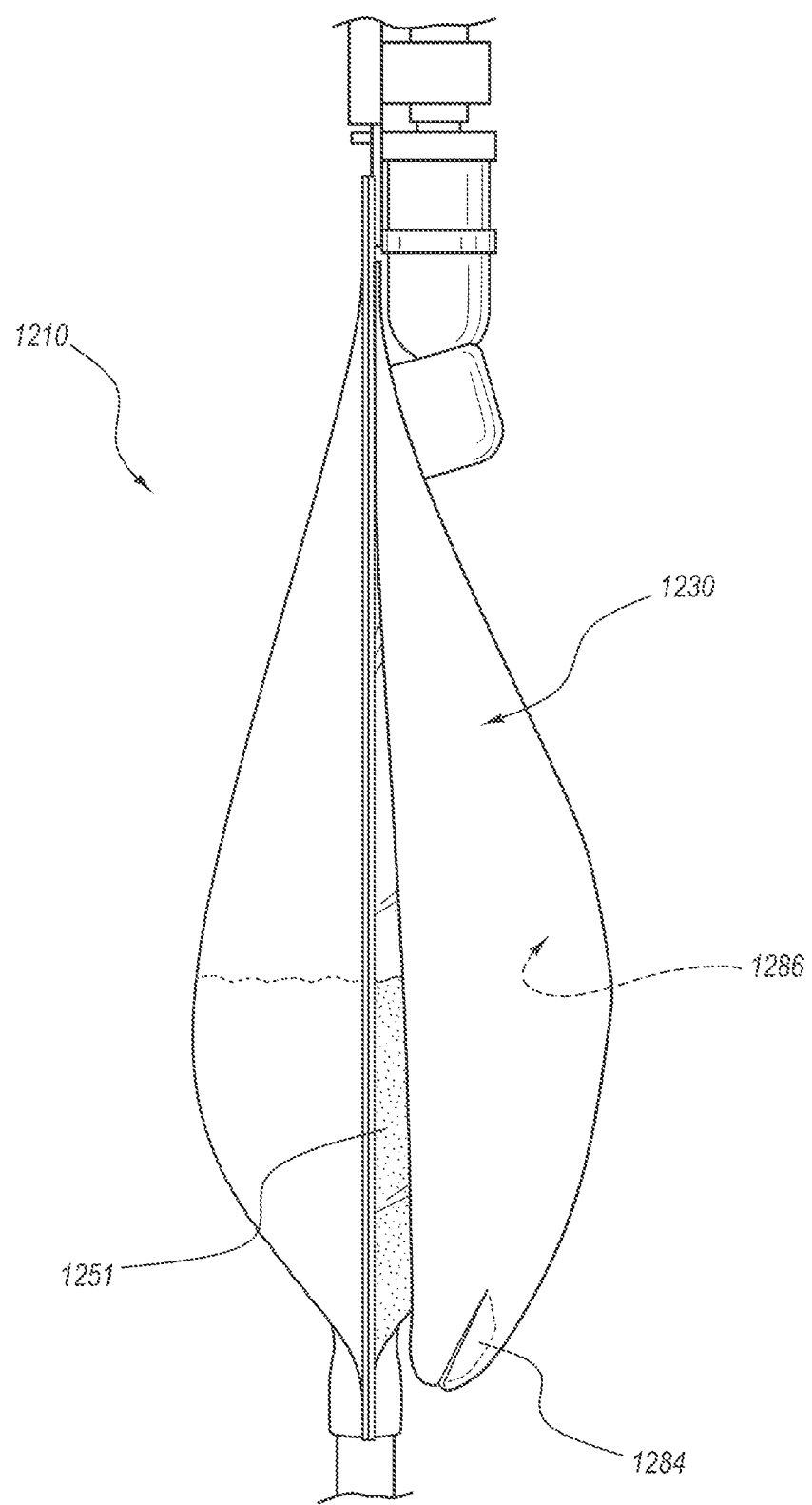
FIG. 22 is a side elevation view of the bodily fluid drainage bag assembly of FIG. 21 with a fluid bag thereof in a partially filled state and the cover thereof in an obscuring orientation.

FIGS. 21 and 22 illustrate another embodiment of a bodily fluid drainage assembly 1200 that includes a fluid bag 1210 and a cover 1230 that resemble the fluid bag 1110 and the cover 1130 just described. However, the cover 1230 is configured to provide better concealment of the fluid bag 1210 for side views, as compared with certain embodiments of the cover 1130. The cover 1230 can include one or more darts or pleats 1284 that draw the cover 1230 into a rounded, cupped, or convex shape (as viewed from the front). In particular, the pleats 1284 can cause the cover 1230 to define a chamber 1286 that is configured to receive a front panel of the bag 1210 as the bag 1210 expands, as shown in FIG. 22. The outer edges of the cover 1230 thus may overlap or curve about the outer edges of the bag 1210 so as to conceal the sides of the expanded bag 1210.

In the illustrated embodiment, the assembly 1200 is shown in an unfilled or pre-use state in FIG. 21, and is shown in a collection or partially filled state in FIG. 22. As can be appreciated from the shading in FIG. 21, the cover 1230 can be non-planar, rounded, or convex when the assembly 1200 is in the pre-use state, as well as when the assembly 1200 is in a collection state (FIG. 22).

In the illustrated embodiment, the pleats are formed by cutting a slit at an angle of about 45 degrees relative to a bottom edge of the cover 1230 at each of the two bottom corners of the cover 1230. The portions of the cover 1230 that neighbor a given slit are then overlapped and joined together in any suitable manner (e.g., via welding, adhesives, etc.). In other embodiments, rather than making a slit at a corner, a small triangular piece may be removed from the corner, and the portions of the cover 1230 that neighbor the resultant gap can then be joined together in any suitable manner.

A variety of other suitable arrangements are possible for the cover 1230. For example, more or fewer pleats 1286 may be used, and one or more of the pleats 1286 may be different sizes and/or positioned at different areas about the cover 1230. In the illustrated embodiment, the contoured cover 1230 is used in place of an obscuring pattern (such as the obscuring pattern 1182 in FIGS. 18 and 20) at the corners of the bag 1230. However, in other embodiments, obscuring patterns may additionally be used.

Figure 23:
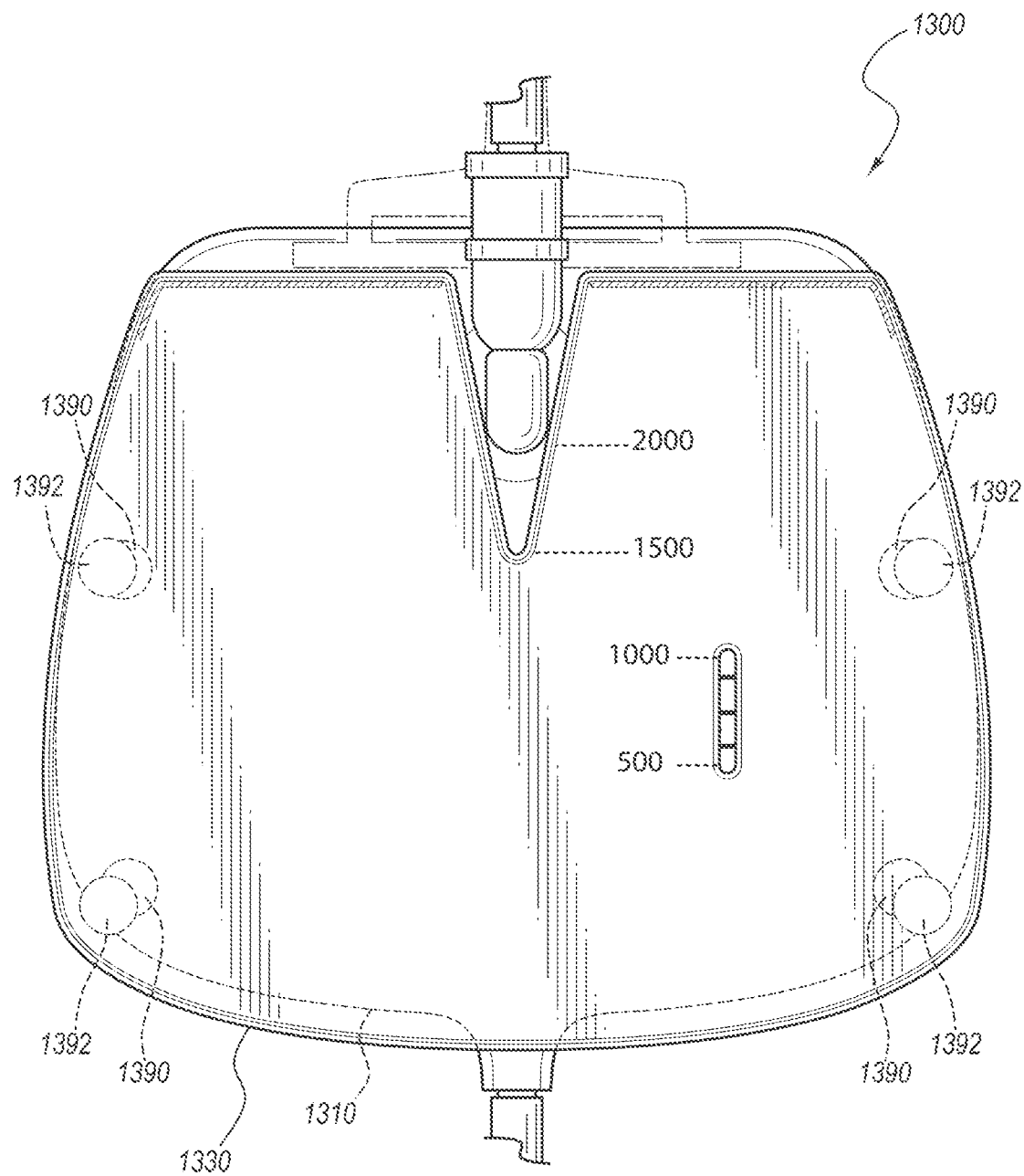
FIG. 23 is a front elevation view of another embodiment of a drainage bag assembly shown in a pre-use state.

FIG. 23 illustrates another embodiment of a bodily fluid drainage assembly 1300 that includes a fluid bag 1310 and a cover 1330. The bag 1310 and the cover 1330 include another mechanism for wrapping the sides of the cover 1330 about the front sides of the bag 1310 so as to conceal a transparent or semitransparent portion of the bag 1310 from side views. In the illustrated embodiment, both the bag 1310 and the cover 1330 include complementary fasteners 1390, 1392 that can be selectively attached to each other so as to conceal the side of a filled or partially filled bag 1310 when the cover 1330 is lowered and in an obscuring orientation. When the fasteners 1390, 1392 are engaged with each other and the bag 1310 is in a partially filled state, the cover 1330 can define a convex shape such as that displayed by the cover 1230 in FIG. 22. The fasteners can be selectively detached from each other so as to permit the cover 1330 to be raised to a viewing orientation. The fasteners can be of any suitable variety (e.g., hook and loop fasteners, snaps, adhesives, etc.). In other embodiments, only one of the bag 1310 and the cover 1330 may include one or more fasteners 1390, 1392 (e.g., resealable adhesives).

A variety of methods for manufacturing and for using bodily fluid drainage assemblies have been discussed in the foregoing disclosure. Various steps and stages of such methods are provided throughout the discussion, such that the overall processes for use and manufacture are evident. Certain illustrative methods for using such an assembly are discussed hereafter, which can serve as an example of the kinds of methods that are evident from the foregoing discussion.

Certain methods of using a bodily fluid drainage assembly include providing a bodily fluid drainage assembly that comprises a fluid bag and a cover, wherein the fluid bag comprises a front face of which at least a portion is transparent or semitransparent, and wherein the cover comprises a first volume indicator. Some methods include hanging the assembly such that the cover is positioned in front of the front face of the fluid bag so as to thereby obscure from view the at least a portion of the front face that is transparent or semitransparent, and such that, from a vantage point in front of the assembly, the cover obscures from view every part of the transparent or semitransparent portion that is not visible through the first volume indicator. Some methods further include coupling the assembly to a patient via a fluid line so as to permit a bodily fluid to collect within the fluid bag. For example, the fluid line 1190 (FIG. 17) may be coupled with a urinary catheter (e.g., Foley catheter) that has been inserted into a patient. The methods can further include determining an approximate volume of bodily fluid that has collected within the fluid bag using the first volume indicator.

In some instances, the cover can be configured to transition between an obscuring orientation and a viewing orientation. In certain of such instances, determining an approximate volume of bodily fluid is performed while the cover is in the obscuring orientation. In various instances, determining an approximate volume of bodily fluid is performed without touching, moving, or lifting the cover.

The first volume indicator can be fixed relative to the cover. For example, the first volume indicator comprises an opening in the cover through which a restricted portion of the front face of the fluid bag is visible when the cover is positioned in front of the front face of the fluid bag. The first volume indicator can comprises a notch (e.g., the cutout 1138) or a window (e.g., the window 118) in the cover. In other instances, the first volume indicator can comprise a fluid level indicator that is printed on the cover (e.g., a fluid level indicator 136, 236).

In some instances, no portion of the front face of the fluid bag is visible through the first volume indicator from a vantage point in front of the assembly when the cover is positioned in front of the front face of the fluid bag. For example, this can be the case where the first volume indicator includes fluid level indicators such as the fluid level indicators 136, 236. In some methods, the assembly comprises an additional cover that cooperates with the volume indicator to provide information regarding an approximate volume of the bodily fluid. In certain of such methods, prior to determining the approximate volume of the bodily fluid that has collected within the fluid bag, the additional cover is permitted to move relative to the volume indicator as the bodily fluid collects within the fluid bag.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. The same is true with respect to the terms such as "second," etc. Moreover, any such reference to a "first," "second," or other numbered item does not necessarily correspond to the "first," "second," or other such numbering of items as set forth in the foregoing description (i.e., the use of such "first," "second," and the like designations is for the sake of convenience and is not necessarily meant to be limiting).

It is believed that one skilled in the art can use the preceding description to utilize the present disclosure to its fullest extent. It will be apparent to those having skill in the art that changes may be made to the details of the above-described embodiments without departing from the underlying principles of the disclosure described herein. In other words, various modifications and improvements of the embodiments specifically disclosed in the description above are within the scope of the appended claims. The scope of the disclosure is therefore defined by the following claims.

The invention claimed is:

1. A urinary drainage bag assembly, comprising:
   a fluid bag including a front panel and a rear panel sealed to each other at or near an outer edge of the fluid bag and having a fillable region and a non-fillable region;
   wherein at least a portion of said front panel includes a substantially transparent or semi-transparent region and a volume indicator comprising graduations indicating predetermined volumes which allow a volume of urine within the fillable region to be determined by a comparison between a top of the urine and the graduations;
   an inlet tube coupled to an upper portion of the fluid bag;
   an outlet tube coupled to a lower portion of the fluid bag;
   a hanger coupled to the upper portion of the fluid bag within the non-fillable region; and
   an opaque fluid bag cover having a top portion and a bottom portion, said cover positioned to obscure a bottom portion of the front panel of the fluid bag including the volume indicator when the cover is in a covered orientation,
   wherein said cover has a cutout that is positioned at a top edge of the cover and that is operable to allow direct viewing of a top edge of the fillable region of the front panel of the fluid bag without moving the cover from the covered orientation, wherein direct viewing of the top edge of the fillable region allows a determination of when the fluid bag is full,
   wherein said cutout is sized to partially surround a junction of the inlet tube and the fluid bag and to obscure the fillable region of the front panel of the fluid bag when said cover is viewed from a forward or side vantage point in the covered orientation,
   wherein said cover is engaged to the fluid bag along a portion of the top edge of the fluid bag, and
   wherein said cover is operable to move from the covered orientation to a viewing orientation to allow direct viewing of a bottom portion of the front panel of the fluid bag upon lifting a bottom edge of the bottom portion of the cover.

2. The urinary drainage bag assembly of claim 1, wherein said cover is operable to allow direct viewing of an entirety of the front panel of the fluid bag upon lifting the cover.

3. The urinary drainage bag assembly of claim 1, wherein said cover is operable to be lifted to reveal at least a portion of the volume indicator.

4. The urinary drainage bag assembly of claim 1, wherein revealing the volume indicator allows the volume of urine in the fluid bag to be determined.

5. The urinary drainage bag assembly of claim 1, wherein said cutout is sized to accommodate a junction of the inlet tube and the fluid bag.

6. The urinary drainage bag assembly of claim 1, wherein said cover is removable from the fluid bag.

7. The urinary drainage bag assembly of claim 1, wherein said cover is removably engaged to the fluid bag by one or more reversible fasteners, including one or more of snaps, hook-and-loop fasteners, adhesives, clips, zippers, resealable adhesives, or combinations thereof.

8. The urinary drainage bag assembly of claim 7, wherein the one or more reversible fasteners are operable to be detached to allow direct viewing of at least a portion of the front panel of the fluid bag.

9. The urinary drainage bag assembly of claim 1, wherein said inlet tube is coupled to the upper portion of the fluid bag with a valve assembly including an anti-reflux valve.

10. The urinary drainage bag assembly of claim 1, wherein said outlet tube includes an output regulator.

11. The urinary drainage bag assembly of claim 1, further comprising an outlet tube holder configured to reversibly retain the outlet tube in at least a partially upright position.

12. The urinary drainage bag assembly of claim 1, wherein a base region of said hanger is coupled within the non-fillable region.

13. The urinary drainage bag assembly of claim 1, wherein said hanger comprises one or more hook-like extensions or apertures.

14. The urinary drainage bag assembly of claim 1, wherein a bottom of said cover extends beyond a bottom edge of the fluid bag.

15. The urinary drainage bag assembly of claim 1, wherein said cover lacks a window.

16. The urinary drainage bag assembly of claim 1, wherein said cover is operable to be displaced in a forward direction from the top portion of the front panel of the fluid bag to allow direct viewing of the top edge of the fillable region of the front panel of the fluid bag.

17. The urinary drainage bag assembly of claim 16, wherein said cover is operable to be displaced in the forward direction from the top edge of the fillable region of the front panel of the fluid bag.

18. The urinary drainage bag assembly of claim 16, wherein said cover is operable to be displaced in the forward direction from the front panel of the fluid bag to reveal at least a portion of the volume indicator.

19. The urinary drainage bag assembly of claim 16, wherein said cover is operable to be displaced in the forward direction from the front panel of the fluid bag to allow direct viewing of the top portion of the front panel of the fluid bag.

\* \* \* \* \*